United States Patent
Yeaman et al.

(10) Patent No.: US 10,653,757 B2
(45) Date of Patent: May 19, 2020

(54) **METHODS AND COMPOSITIONS FOR VACCINATING AGAINST *STAPHYLOCOCCUS AUREUS***

(75) Inventors: Michael R. Yeaman, Redondo Beach, CA (US); John E. Edwards, Jr., Palos Verdes Estates, CA (US); Scott G. Filler, Rancho Palos Verdes, CA (US); Ashraf S. Ibrahim, Irvine, CA (US); Yue Fu, Carson, CA (US); John P. Hennessey, Jr., Lower Gwynedd, PA (US)

(73) Assignees: NovaDigm Therapeutics, Inc., Grand Forks, ND (US); Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 0 days.

(21) Appl. No.: 14/234,269

(22) PCT Filed: Jul. 20, 2012

(86) PCT No.: PCT/US2012/000328
§ 371 (c)(1),
(2), (4) Date: Jun. 8, 2015

(87) PCT Pub. No.: WO2013/015831
PCT Pub. Date: Jan. 31, 2013

(65) Prior Publication Data
US 2015/0273031 A1    Oct. 1, 2015

Related U.S. Application Data

(60) Provisional application No. 61/510,896, filed on Jul. 22, 2011.

(51) Int. Cl.
| | | |
|---|---|---|
| *A61K 39/00* | (2006.01) | |
| *A61K 39/09* | (2006.01) | |
| *A61K 39/085* | (2006.01) | |
| *A01N 63/04* | (2006.01) | |
| *A61K 36/06* | (2006.01) | |
| *A61K 45/06* | (2006.01) | |

(52) U.S. Cl.
CPC .......... *A61K 39/0002* (2013.01); *A61K 45/06* (2013.01); *A61K 2039/55505* (2013.01); *A61K 2039/58* (2013.01)

(58) Field of Classification Search
CPC .... A61K 39/0002; A61K 36/06; A61K 35/66; A61K 2039/58; A61K 2039/55505; A61K 45/06; C07K 16/1271
See application file for complete search history.

(56) References Cited

U.S. PATENT DOCUMENTS

| | | |
|---|---|---|
| 4,346,074 A | 8/1982 | Gilmour et al. |
| 5,578,309 A | 11/1996 | Cutler et al. |
| 5,622,939 A | 4/1997 | Jamas et al. |
| 5,668,263 A | 9/1997 | Hoyer et al. |
| 5,817,466 A | 10/1998 | Hoyer et al. |
| 5,961,970 A | 10/1999 | Lowell et al. |
| 6,248,329 B1 | 6/2001 | Chandrashekar et al. |
| 6,703,025 B1 | 3/2004 | Patti et al. |
| 6,747,137 B1 | 6/2004 | Weinstock et al. |
| 7,067,138 B1 | 6/2006 | Edwards, Jr. et al. |
| 7,241,613 B1 | 7/2007 | Willins et al. |
| 7,250,286 B2 | 7/2007 | Ellison |
| 7,666,438 B1 | 2/2010 | Patti et al. |
| 7,732,187 B2 | 6/2010 | Cochran et al. |
| 8,541,008 B2 | 9/2013 | Edwards, Jr. et al. |
| 2002/0102262 A1 | 8/2002 | Hook et al. |
| 2002/0146435 A1 | 10/2002 | Evans et al. |
| 2003/0124134 A1 | 7/2003 | Edwards et al. |
| 2003/0217373 A1 | 11/2003 | Green et al. |
| 2004/0116380 A1 | 6/2004 | Jamas et al. |
| 2004/0175731 A1 | 9/2004 | Pier et al. |
| 2005/0287146 A1 | 12/2005 | Patti et al. |
| 2006/0083750 A1 | 4/2006 | Edwards et al. |
| 2007/0077256 A1 | 4/2007 | Edwards et al. |
| 2008/0311135 A1 | 12/2008 | Zheng et al. |
| 2009/0297562 A1 | 12/2009 | Edwards et al. |
| 2010/0015182 A1 | 1/2010 | Lang et al. |

(Continued)

FOREIGN PATENT DOCUMENTS

| | | |
|---|---|---|
| EP | 2428800 A1 | 3/2012 |
| JP | 2007-512312 A | 5/2007 |

(Continued)

OTHER PUBLICATIONS

Rudinger et al. In: Peptide Hormones. (Ed) JA Parsons, University Park Press, pp. 1-7, 1976.*

(Continued)

*Primary Examiner* — Gary B Nickol
*Assistant Examiner* — Lakia J Jackson-Tongue
(74) *Attorney, Agent, or Firm* — Clark & Elbing LLP

(57) ABSTRACT

The invention features a method of vaccinating a mammal against *Staphylococcus aureus* which includes the steps of: a) identifying a mammal at risk for the development of a *Staphylococcus aureus* skin or soft tissue infection; and b) administering to said mammal an immunogenic amount of a vaccine that includes a polypeptide including an isolated agglutinin-like sequence (Als) 3 protein (Als3p), or an immunogenic fragment thereof, in a pharmaceutically acceptable medium.

17 Claims, 14 Drawing Sheets

(7 of 14 Drawing Sheet(s) Filed in Color)

Specification includes a Sequence Listing.

(56) References Cited

U.S. PATENT DOCUMENTS

| | | | |
|---|---|---|---|
| 2010/0150942 A1 | 6/2010 | Cantor | |
| 2010/0150956 A1 | 6/2010 | Patti et al. | |
| 2010/0285109 A1* | 11/2010 | Zurbriggen | C12N 9/6478 424/450 |
| 2012/0014995 A1 | 1/2012 | Edwards, Jr. et al. | |
| 2012/0107316 A1 | 5/2012 | Cassone et al. | |
| 2012/0237534 A1 | 9/2012 | Fu et al. | |
| 2014/0037689 A1* | 2/2014 | Edwards, Jr. | A61K 39/0002 424/274.1 |
| 2014/0335114 A1 | 11/2014 | Fu et al. | |
| 2016/0220648 A1 | 8/2016 | Edwards, Jr. et al. | |

FOREIGN PATENT DOCUMENTS

| | | |
|---|---|---|
| JP | 2009-524601 A | 7/2009 |
| JP | 2012-530786 A | 12/2012 |
| WO | WO-2005/049081 A1 | 6/2005 |
| WO | WO-2006/036817 A2 | 4/2006 |
| WO | WO-2006/059228 A2 | 6/2006 |
| WO | WO-2006/121895 A2 | 11/2006 |
| WO | WO-2007/081896 A2 | 7/2007 |
| WO | WO-2007/126813 A2 | 11/2007 |
| WO | WO-2010/151544 A1 | 12/2010 |
| WO | WO-2011/003085 A1 | 1/2011 |
| WO | WO-2012/163533 A1 | 12/2012 |
| WO | WO-2013/015831 A1 | 1/2013 |
| WO | WO-2016/142660 A1 | 9/2016 |
| WO | WO-2017/155949 A1 | 9/2017 |

OTHER PUBLICATIONS

Barki et al., "Isolation of a Candida albicans DNA sequence conferring adhesion and aggregation on Saccharomyces cerevisiae," J Bacteriol. 175(17):5683-9 (1993).

Bendel et al., "Distinct mechanisms of epithelial adhesion for Candida albicans and Candida tropicalis. Identification of the participating ligands and development of inhibitory peptides," J Clin Invest. 92(4):1840-9 (1993).

Caesar-TonThat et al., "A monoclonal antibody to Candida albicans enhances mouse neutrophil candidacidal activity," Infect Immun. 65(12):5354-7 (1997).

Castaldo et al., "Clinical spectrum of fungal infections after orthotopic liver transplantation," Arch Surg. 126(2):149-56 (1991).

Cheng et al, "Comparison between Candida albicans agglutinin-like sequence gene expression patterns in human clinical specimens and models of vaginal candidiasis, " Infect Immun. 73(3):1656-63 (2005).

Choi et al., "Acinetobacter baumanni invades epithelial cells and outer membrane protein A mediates interactions with epithelial cells," BMC Microbiol. 8:216 (2008) (11 pages).

Coleman et al., "Monoclonal antibodies specific for Candida albicans Als3 that immunolabel fungal cells in vitro and in vivo and block adhesion to host surfaces," J Microbiol Methods. 78(1):71-8 (2009) (19 pages).

Communication from the Examining Division and Annex to the Communication issued in Europoean Patent Application No. 11008862.2 dated Apr. 23, 2014 (6 pages).

Cormack et al., "An adhesion of the yeast pathogen Candida glabrata mediating adherence to human epithelial cells," Science. 285(5427):578-82 (1999).

Cutler et al., "Characteristics of Candida albicans adherence to mouse tissues," Infect Immun. 58(6):1902-8 (1990).

De Bernardis et al., "Protective role of antimannan and anti-aspartyl proteinase antibodies in an experimental model of Candida albicans vaginitis in rats," Infect Immun. 65(8):3399-405 (1997).

Santoni, "Intravaginal and intranasal immunizations confer equal protection against Candida in experimental vaginitis," Abstracts of the General Meeting of the American Society for Microbiology 101:367-8 (2001) (3 pages).

Dromer et al., "Protection of mice against experimental cryptococcosis by anti-Cryptococcus neoformans monoclonal antibody," Infect Immun. 55(3):749-52 (1987).

Ekenna et al., "Natural history of bloodstream infections in a burn patient population: the importance of candidemia," Am J Infect Control. 21(4):189-95 (1993).

Ellis, Chapter 29: New technologies for making vaccines. *Vaccines.* (Eds) Plotkin and Mortimer, W.B. Saunders Company, Philadelphia, 568-575 (1988).

English Language Translation of Notice of Final Rejection issued in Japanese Patent Application No. 2008-549598, dated Feb. 21, 2013, dated Feb. 25, 2013 (5 pages).

English Language Translation of Notice of Reasons for Rejection issued in Japanese Patent Application No. 2008-549598, dated Mar. 15, 2012, dated Mar. 21, 2012 (9 pages).

English Translation of Official Communication for Japanese Patent Application No. 2008-510281, dated Dec. 12, 2011 (3 pages).

Examiner's First Report for Australian Patent Application No. 2006244401, dated Nov. 25, 2010 (1 page).

Examiner's Report for Canadian Patent Application No. 2,636,277, dated May 13, 2014 (2 pages).

Examiner's Report issued in Canadian Patent Application No. 2,607,176, dated Nov. 26, 2012 (3 pages).

Examiner's Report issued in Canadian Patent Application No. 2,636,277, dated Dec. 4, 2012 (5 pages).

Extended European Search Report for EP Patent Application No. 07709622.0, dated Nov. 19, 2009 (9 pages).

Extended European Search Report for European Application No. 06752341.5, dated Nov. 13, 2009 (15 pages).

Extended European Search Report for European Patent Application No. 11008862.2, dated Feb. 10, 2012 (10 pages).

Extended European Search Report for European Patent Application No. 12001586.2, dated Nov. 13, 2012 (14 pages).

Extended European Search Report for European Patent Application No. 12001595.3, dated Nov. 13, 2012 (12 pages).

Extended European Search Report for European Patent Application No. 12832321.9, dated Jun. 3, 2015 (9 pages).

Filler, "Candida-host cell receptor-ligand interactions," Curr Opin Microbiol. 9(4):333-9 (2006).

Final Japanese Office Action for Japanese Patent Application No. 2008-510281, dated Oct. 26, 2012 (3 pages).

Final Japanese Office Action for Japanese Patent Application No. 2008-549598, dated Feb. 25, 2013 (5 pages).

Final Japanese Office Action for Japanese Patent Application No. 2012-207831, dated Dec. 16, 2014 (10 pages).

First Exam Report for EP Patent Application No. 06752341.5, dated Feb. 18, 2010 (8 pages).

First Examiner's Report issued in Australian Patent Application No. 2007205065, dated Jan. 18, 2012 (2 pages).

Fisher-Hoch et al., "Opportunistic candidiasis: an epidemic of the 1980's," Clin Infect Dis. 21(4):897-904 (1995).

Fonzi et al., "Isogenic strain construction and gene mapping in Candida albicans," Genetics. 134(3):717-28 (1993).

Fu et al., "Candida albicans Als1p: an Adhesin that is a Downstream Effector of the EFG1 Filamentation Pathway," Mol Microbiol. 44(1):61-72 (2002).

Fu et al., "Cloning and characterization of a gene (LIP1) which encodes a lipase from the pathogenic yeast Candida albicans," Microbiology. 143(Pt 2):331-40 (1997).

Fu et al., "Cloning and characterization of CAD1/AAF1, a gene from Candida albicans that induces adherence to endothelial cells after expression in Saccharomyces cerevisiae," Infect Immun. 66(5):2078-84 (1998).

Fu et al., "Expression of the Candida albicans Gene ALS1 in Saccharomyces cerevisiae Induces Adherence to Endothelial and Epithelial Cells," Infect Immun. 66(4):1783-6 (1998).

Gale et al., "Cloning and expression of a gene encoding an integrin-like protein in Candida albicans," Proc Nat Acad Sci USA. 93(1):357-61 (1996).

Gale et al., "Linkage of adhesion, filamentous growth, and virulence in Candida albicans to a single gene, INT1," Science. 279(5355):1355-8 (1998).

(56) References Cited

OTHER PUBLICATIONS

Gaur et al., "Expression, cloning, and characterization of a Candida albicans gene, ALA1, that confers adherence properties upon Saccharomyces cerevisiae for extracellular matrix proteins," Infect Immun. 65(12):5289-94 (1997).
Gietz et al., "Studies on the transformation of intact yeast cells by the LiAc/SS-DNA/PEG procedure," Yeast. 11(4):355-60 (1995).
Greenspan et al., "Defining epitopes: It's not as easy as it seems," Nat Biotechnol. 7(10):936-7 (1999).
Gustafson et al., "Molecular mimicry in Candida albicans. Role of an integrin analogue in adhesion of the yeast to human endothelium," J Clin Invest. 87(6):1896-902 (1991).
Han et al., "Antibody response that protects against disseminated candidiasis," Infect Immun. 63(7):2714-9 (1995).
Hasenclever et al., "Antigenic relationships of Torulopsis glabrata and seven species of the genus Candida," J Bacteriol. 79:677-81 (1960).
Hoyer et al., "Candida albicans ALS1: Domains Related to a Saccharomyces cerevisiae Sexual Agglutinin Separated by a Repeating Motif," Mol Microbiol. 15(1):39-54 (1995).
Hoyer et al., "Candida albicans ALS3 and Insights Into the Nature of the ALS Gene Family," Curr Genet. 33(6):451-9 (1998).
Hoyer et al., "Characterization of agglutinin-like sequence genes from non-albicans candida and phylogenetic analysis of the ALS family," Genetics. 157(4):1555-67 (2001).
Hoyer et al., "Detection of Als Proteins on the Cell Wall of Candida albicans in Murine Tissues," Infect Immun. 67(8):4251-55 (1999).
Hoyer et al., "Identification of Candida albicans ALS2 and ALS4 and localization of als proteins to the fungal cell surface," J Bacteriol. 180(20):5334-43 (1998).
Hoyer, "The ALS Gene Family of Candida albicans," Trends Microbiol. 9(4):176-80 (2001).
Ibrahim et al., "Evidence implicating phospholipase as a virulence factor of Candida albicans," Infect Immun. 63(5):1993-8 (1995).
Ibrahim et al., "The Anti-Candida Vaccine Based on the Recombinant N-Terminal Domain of Als1p Is Broadly Active against Disseminated Candidiasis," Infect Immun. 74(5):3039-41 (2006).
Ibrahim et al., "Vaccination with Recombinant N-Terminal Domain of Als1p Improves Survival during Murine Disseminated Candidiasis by Enhancing Cell-Mediated, Not Humoral, Immunity," Infect Immun. 73(2):999-1005 (2005).
Illustrated Stedman's Medical Dictionary, 24th Edition, Williams and Wilkins, Londin, p. 707 (1982).
Inhibitex reports favorable results from aurexis phase II trial for the treatment of staph bloodstream infections. Inhibitex Inc. (2005) (Accessed Sep. 19, 2005) (5 pages).
International Preliminary Report on Patentability and Written Opinion for International Application No. PCT/US2012/055604, dated Mar. 18, 2014 (11 pages).
International Preliminary Report on Patentability for International Application No. PCT/US2006/017482, dated Nov. 6, 2007 (4 pages).
International Preliminary Report on Patentability for International Application No. PCT/US2007/000433, dated Jul. 8, 2008 (5 pages).
International Search Report and Written Opinion for International Application No. PCT/US06/17482, dated Mar. 19, 2007 (5 pages).
International Search Report for International Patent Application No. PCT/US07/00433, dated Oct. 1, 2007 (1 page).
International Search Report for International Patent Application No. PCT/US12/55604, dated Mar. 8, 2013 (17 pages).
International Search Report of International Application No. PCT/US12/00328, dated Dec. 18, 2012 (3 pages).
Jaffe et al., "Culture of human endothelial cells derived from umbilical veins. Identification by morphologic and immunologic criteria," J Clin Invest. 52(11):2745-56 (1973).
Japanese Inquiry Rejection for Japanese Patent Application No. 2008-549598, dated Mar. 7, 2014 (13 pages).
Japanese Office Action for Japanese Patent Application No. 2014-105980, dated Apr. 24, 2015 (2 pages).
Jarvis et al., "Predominant pathogens in hospital infections," J Antimicrob Chemother. 29 (Suppl A): 19-24 (1992).
Jimenez-Lucho et al., "Cryptococcus neoformans, Candida albicans, and other fungi bind specifically to the glycosphingolipid lactosylceramide (Galβ1-4Glcβ1-1Cer), a possible adhesion receptor for yeasts," Infect Immun. 58(7):2085-90 (1990).
Kim et al., "Partial characterization of leukocyte binding molecules on endothelial cells induced by minimally oxidized LDL," Arterioscler Thromb. 14(3):427-33 (1994).
Klein et al., "Role of cell surface molecules of Blastomyces dermatitidis in the pathogenesis and immunobiology of blastomycosis," Semin Respir Infect. 12(3):198-205 (1997).
Klotz et al., "Effect of an arginine-glycine-aspartic acid-containing peptide on hematogenous candidal infections in rabbits," Antimicrob Agents Chemother. 36(1):132-6 (1992).
Kramer et al., "How long do nosocomial pathogens persist on inanimate surfaces? A systematic review," BMW Infect Dis. 6:130 (2006) (8 pages).
Lipke et al., "AG alpha 1 is the structural gene for the Saccharomyces cerevisiae alpha-agglutinin, a cell surface glycoprotein involved in cell-cell interactions during mating," Mol Cell Biol. 9(8):3155-65 (1989).
Liu et al., "INH-A21 contains antibodies specific for the Candida ALS protein family," 44th ICAAC Abstracts, Washington D.C. p. 425, M-1144, Oct. 30-Nov. 2, 2004 (1 page).
Lotter et al., "Identification of an epitope on the Entamoeba histolytica 170-kD lectin conferring antibody-mediated protection against invasive amebiasis," J Exp Med. 185(10):1793-801 (1997).
Loza et al., "Functional Analysis of the Candida albicans ALS1 Gene Product," Yeast 21(6):473-82 (2004).
Luo et al., "Candida albicans Hyr1p confers resistance to neutrophil killing and is a potential vaccine target," J Infect Dis. 201(11):1718-28 (2010) (18 pages).
Luo et al., "Active and passive immunization with rHyr1p-N protects mice against hematogenously disseminated candidiasis," PloS One. 6(10):e25909 (2011) (8 pages).
Mamo et al., "Protection Induced in Mice Vaccinated with Recombinant Collagen-Binding Protein (CnBP) and Alpha-Toxoid against Intramammary Infection with *Staphylococcus aureus*," Microbiol Immunol. 44(5):381-4 (2000).
Mamo et al., "Vaccination against *Staphylococcus aureus* mastitis: immunological response of mice vaccinated with fibronectin-binding protein (FnBP-A) to challenge with S.aureus," Vaccine. 12(11):988-92 (1994).
Mamo et al., "Vaccination with *Staphylococcus aureus* fibrinogen binding proteins (FgBPs) reduces colonisation of S. aureus in a mouse mastitis model," FEMS Immonol Med Microbiol. 10(1):47-53 (1994).
Manjarrez-Hernandez et al., "Binding of diarrheagenic *Escherichia coli* to 32- to 33-kilodalton human intestinal brush border proteins," Infect Immun. 65(11):4494-501 (1997).
Mayer et al., "Candida albicans adherence to endothelial cells," Microvasc Res. 43(2):218-26 (1992).
Mayer et al., "Recognition of binding sites on Candida albicans by monoclonal antibodies to human leukocyte antigens," Infect Immun. 58(11):3765-9 (1990).
Mukherjee et al., "Protective murine monoclonal antibodies to Cryptococcus neoformans," Infect Immun. 60(11):4534-41 (1992).
NCBI Blast for Accession No. YP_001084998. Retrieved on Nov. 27, 2012 (2 pages).
Nilsson et al., "Vaccination with a Recombinant Fragment of Collagen Adhesin Provides Protection against *Staphylococcus Aureus*-mediated Septic Death," J Clin Invest. 101(12):2640-9 (1998).
Notice of Reasons for Rejection for Japanese Patent Application No. 2008-549598, dated Mar. 21, 2012 (15 pages).
Notice of Reasons for Rejection for Japanese Patent Application No. 2012-207831, dated Nov. 22, 2013 (15 pages).
Office Action for European Patent Application No. 07709622.0, dated Jan. 27, 2012 (8 pages).
Office Communication for EP Patent Application No. 07709622.0, dated Nov. 17, 2010 (12 pages).
Office Communication for EP Patent Application No. 07709622.0, dated Mar. 3, 2010 (6 pages).
Official Communication and Annex for European Patent Application No. 07709622.0, dated Jun. 30, 2011 (4 pages).

(56) References Cited

OTHER PUBLICATIONS

Oh et al., "Functional specificity of Candida albicans Als3p proteins and clade specificity of ALS3 alleles discriminated by the number of copies of the tandem repeat sequence in the central domain," Microbiology. 151(Pt 3):673-81 (2005).
Opal et al., "Systemic host responses in severe sepsis analyzed by causative microorganism and treatment effects of drotrecogin alfa (activated)," Clin Infect Dis. 37(1):50-8 (2003).
Palaszynski et al., "Systemic immunization with conserved pilus-associated adhesins protects against mucosal infections," Dev Biol Stand. 92:117-22 (1998).
Panaretou et al., Chapter 13:Isolation of yeast plasma membranes. *Methods in Molecular Biology, vol. 53: Yeast Protocols*. I.H. Evans (ed.), Humana Press, Totowa, New Jersey, 117-21 (1996).
Patent Examination Report No. 2 for Australian Patent Application No. 2006244401, dated Aug. 21, 2012 (3 pages).
Patent Examination Report No. 2 issued in Australian Patent Application No. 2007205065, dated Mar. 12, 2013 (3 pages).
Patent Examination Report No. 3 issued in Australian Patent Application No. 2007205065, dated Oct. 15, 2013 (3 pages).
Patent Examination Report No. 1 issued in Australian Patent Application No. 2013203750, dated Aug. 20, 2014 (4 pages).
Patti et al., "MSCRAMM-mediated adherence of microorganisms to host tissues," Annu Rev Microbiol. 48:585-617 (1994).
Patti, "Vaccines and immunotherapy for staphylococcal infections," Int J Artif Organs. 28(11):1157-62 (2005).
Peleg et al., "Prokaryote-eukaryote interactions identified by using Caenorhabditis elegans," Proc Natl Acad Sci USA. 105(38):14585-90 (2008).
Perraut et al., "Successful treatment of Candida albicans endophthalmitis with intravitreal amphotericin B," Arch Opthalmol. 99(9):1565-7 (1981).
Pfaller et al., "National surveillance of nosocomial blood stream infection due to species of Candida other than Candida albicans: frequency of occurrence and antifungal susceptibility in the SCOPE Program. SCOPE Participant Group. Surveillance and Control of Pathogens of Epidemiologic," Diagn Microbiol Infect Dis. 30(2):121-9 (1998).
Pietrella et al., "A beta-glucan-conjugate vaccine and anti-beta-glucan antibodies are effective against murine vaginal candidiasis as assessed by a novel in vivo imaging technique," Vaccine. 28(7):1717-25 (2010).
Polak, "Combination therapy of experimental candidiasis, cryptococcosis, aspergillosis and wangiellosis in mice," Chemotherapy. 33(5):381-95 (1987).
Prasadarao et al., "Identification and characterization of S fimbria-binding sialoglycoproteins on brain microvascular endothelial cells," Infect Immun. 65(7):2852-60 (1997).
Rieg et al., "Unanticipated heterogeneity in growth rate and virulence among Candida albicans AAF1 null mutants," Infect Immun. 67(7):3193-8 (1999).
Rotrosen et al., "Adherence of Candida to cultured vascular endothelial cells: mechanisms of attachment and endothelial cell penetration," J Infect Dis. 152(6):1264-74 (1985).
Sanford et al., "Passive immunization against Cryptococcus neoformans with an isotype-switch family of monoclonal antibodies reactive with cryptococcal polysaccharide," Infect Immun. 58(6):1919-23 (1990).
Sanger et al., "A rapid method for determining sequences in DNA by primed synthesis with DNA polymerase," J Mol Biol. 94(3):441-8 (1975).
Saporito-Irwin et al., "PHR1, a pH-regulated gene of Candida albicans, is required for morphogenesis," Mol Cell Biol. 15(2):601-13 (1995).
Schmidt et al., "NDV-3, a recombinant alum-adjuvanted vaccine for Candida and *Staphylococcus aureus* is safe and immunogenic in healthy adults," Vaccine. 30(52):7594-600 (2012) (18 pages).
Schnaar, "Isolation of glycosphingolipids," Methods Enzymol. 230:348-70 (1994).
Search Information Statement for Australian Patent Application No. 2006244401, dated Nov. 24, 2010 (3 pages).
Segal et al.,"Protection against systemic infections with various Candida species elicited by vaccination with Candida albicans ribosomes," Sabouraudia. 23(4):275-85 (1985).
Sheppard et al., "Functional and structural diversity in the Als protein family of Candida albicans," J Biol Chem. 279(29):30480-9 (2004).
Sheth et al., "Development of an anti-adhesive vaccine for Pseudomonas aeruginosa targeting the c-terminal region of the pilin structural protein," Biomed Pept Proteins Nucleic Acids. 1(3):141-8 (1995).
Smith et al.,"New insights into Acinetobacter baumannii pathogenesis revealed by high-density pyrosequencing and transposon mutagenesis," Genes Dev. 21(5):601-14 (2007).
Soares et al.,"2-DE analysis indicates that Acinetobacter baumannii displays a robust and versatile metabolism," Proteome Sci. 7:37 (2009) (10 pages).
Spellberg et al., "Current treatment strategies for disseminated candidiasis," Clin Infect Dis 42(2):244-51 (2006).
Spellberg et al., "Efficacy of the Anti-Candida rAls3p-N or rAls1p-N Vaccines against Disseminated and Mucosal Candidiasis," J Infect Dis 194(2):256-60 (2006).
Spellberg et al., "Parenchymal organ, and not splenic, immunity correlates with host survival disseminated candidiasis," Infect Immun. 71(10):5756-64 (2003).
Spellberg et al., "The Antifungal Vaccine Derived from the Recombinant N Terminus of Als3p Protects Mice against the Bacterium *Staphylococcus aureus*," Infect Immun. 76(10):4574-80 (2008).
Spellberg et al., "The pathophysiology and treatment of Candida sepsis," Curr Infect Dis Rep. 4(5):387-99 (2002).
Spellberg et eal., "Mice with disseminated candidiasis die of progressive sepsis," J Infect Dis. 192(2):336-43 (2005).
Stuehler et al.,"Cross-protective TH1 immunity against Aspergillus fumigatus and Candida albicans," Blood. 117(22):5881-91 (2011).
Sundstrom, "Adhesion in Candida spp," Cell Microbiol. 4(8):461-9 (2002).
Supplementary European Search Report for European Application No. 06752341.5, dated Nov. 13, 2009 (15 pages).
Supplementary European Search Report for European Patent Application No. 07709622.0, dated Nov. 19, 2009 (9 pages).
The Webster's II New Riverside Dictionary, The Riverside Publishing Company, p. 933 (1984).
Translation of Cited Reference 3: Today's Therapy 2002, Igaku-Shoin Ltd., p. 155-156 from Japanese Application No. 2012-207831 (5 pages).
Translation of Cited Reference 2: Today's Therapy 2004, Igaku-Shoin Ltd, p. 166 from Japanese Application No. 2012-207831 (5 pages).
von Eiff et. al., "Distribution of capsular and surface polysaccharide serotypes of *Staphylococcus aureus*," Diagn Microbiol Infect Dis. 58(3):297-302 (2007).
Wenzel et al., "Candida species: emerging hospital bloodstream pathogens [editoral]," Infect Control Hosp Epidermiol. 12(9):523-4 (1991).
Wey et al., "Hospital-acquired candidemia. The attributable mortality and excess length of stay," Arch Intern Med. 148(12):2642-5 (1988).
Wisplinghoff et al., "Nosocomial bloodstream infections in US hospitals: analysis of 24,179 cases from a prospective nationwide surveillance study," Clin Infect Dis. 39(3):309-17 (2004).
Wojciechowicz et al., "Cell surface anchorage and ligand-binding domains of the Saccharomyces cerevisiae cell adhesion protein alpha-agglutinin, a member of the immunoglobulin superfamily," Mol Cell Biol. 13(4):2554-63 (1993).
Written Opinion for International Application No. PCT/US07/00433, dated Oct. 1, 2007 (4 pages).
Xiong et al., "New Approaches to the Prevention and Treatment of Severe S. Aureus Infections," Drugs Today (Barc). 36(8):529-39 (2000).
Yan et al., "Hemoglobin-induced binding of Candida albicans to the cell-binding domain of fibronectin is independent of the Arg-Gly-Asp sequence," Infect Immun. 66(5):1904-9 (1998).

(56) References Cited

OTHER PUBLICATIONS

Yeaman et al., "Mechanisms of NDV-3 vaccine efficacy in MRSA skin versus invasive infection," Proc Natl Acad Sci USA. 111(51):E5555-63 (2014).
Zhao et al., "Allelic variation in the contiguous loci encoding Candida albicans ALS5, ALS1 and ALS9," Microbiology. 149(Pt 10):2947-60 (2003).
Zhao et al., "ALS3 and ALS8 represent a single locus that encodes a Candida albicans adhesion; functional comparisons between Als3p and Als1p," Microbiology. 150(Pt 7):2415-28 (2004).
Zhao et al., "Analysis of the candida albicans Als2p and Als4p adhesins suggests the potential for compensatory function within the Als family," Microbiology. 151(Pt 5):1619-30 (2005).
Finks et al., "Vancomycin-resistant *Staphylococcus aureus*, Michigan, USA, 2007" Emerg Infect Dis. 15(6):943-945 (2009).
International Search Report for International Application No. PCT/US2012/00328, dated Dec. 18, 2012 (3 pages).
International Preliminary Report on Patentability for International Patent Application No. PCT/US2012/000328, dated Jan. 28, 2014 (6 pages).
Written Opinion of the International Searching Authority for International Application No. PCT/US2012/00328, dated Dec. 18, 2012 (5 pages).
Supplementary European Search Report for European Patent Application No. 12817530.4, dated Dec. 18, 2014 (7 pages).
Notification of the First Office Action for Chinese Patent Application No. 2012800463214, dated Jan. 19, 2015 (English language translation included) (20 pages).
Liang et al., "Prediction of antigenic epitopes on protein surfaces by consensus scoring," BMC Bioinformatics. 10:302 (2009) (10 pages).
GenBank AAO72958.1. Retrieved on Jan. 6, 2016 (2 pages).
International Search Report for International Patent Application No. PCT/US2014/28535, dated Oct. 24, 2014 (5 pages).
Written Opinion of the International Searching Authority for International Patent Application No. PCT/US2014/28535, dated Oct. 24, 2014 (6 pages).
International Preliminary Report on Patentability for International Patent Application No. PCT/US2014/28535, dated Sep. 15, 2015 (7 pages).
International Search Report for International Patent Application No. PCT/US2014/28521, dated Nov. 13, 2014 (7 pages).
Written Opinion of the International Searching Authority for International Patent Application No. PCT/US2014/28521, dated Nov. 13, 2014 (10 pages).
International Preliminary Report on Patentability for International Patent Application No. PCT/US2014/28521, dated Oct. 13, 2015 (11 pages).
International Search Report for International Patent Application No. PCT/US2014/28256, dated Aug. 18, 2014 (4 pages).
Written Opinion of the International Searching Authority for International Patent Application No. PCT/US2014/28256, dated Aug. 18, 2014 (6 pages).
International Preliminary Report on Patentability for International Patent Application No. PCT/US2014/28256, dated Sep. 15, 2015 (7 pages).
Second Office Action for Chinese Patent Application No. 201280046321.4, dated Oct. 26, 2015 (14 pages) (English language translation provided).
Summons to attend oral proceedings pursuant to Rule 115(1) EPC for European Patent Application No. 11008862.2, dated Oct. 20, 2015 (6 pages).
Summons to attend oral proceedings pursuant to Rule 115(1) EPC for European Patent Application No. 12001586.2, dated Oct. 19, 2015 (7 pages).
Notification of Reason for Rejection for Japanese Patent Application No. 2014-105980, dated Jan. 29, 2016 (13 pages) (English language translation provided).
Office Action for Georgian Patent Application No. 13226/01, dated Feb. 9, 2015 (2 pages) (English language translation provided).
Office Action for Ukrainian Patent Application No. a 2013 10981, dated Nov. 13, 2015 (6 pages) (English translation provided).
Notice of Reasons for Rejection for Japanese Patent Application No. 2015-018131, dated Mar. 16, 2016 (9 pages) (English language translation provided).
Lin et al., "Acinetobacter baumannii rOmpA vaccine dose alters immune polarization and immunodominant epitopes," Vaccine. 31(2):313-8 (2013).
First Office Action for Chinese Patent Application No. 2012800560182, dated Mar. 14, 2016 (27 pages) (English language translation provided).
Notice of Reasons for Rejection for Japanese Patent Application No. 2014-521610, dated Apr. 20, 2016 (11 pages) (English language translation provided).
Communication pursuant to Article 94(3) EPC for European Patent Application No. 12817530.4, dated Jul. 6, 2017 (7 pages).
Miller et al., "Immunity against *Staphylococcus aureus* cutaneous infections," Nat Rev Immunol. 11(8):505-18 (2011).
Communication pursuant to Article 94(3) EPC for European Patent Application No. 12817530.4, dated May 7, 2018 (7 pages).
International Search Report for International Application No. PCT/US2018/026889, dated Jul. 11, 2018 (4 pages).
Written Opinion of the International Searching Authority for International Application No. PCT/US2018/026889, dated Jul. 11, 2018 (13 pages).
Chowdhary et al., "Candida auris: A rapidly emerging cause of hospital-acquired multidrug-resistant fungal infections globally," PLoS Pathog. 13(5):e1006290 (2017) (10 pages).
Kaur et al., "Strategies to reduce mortality in adult and neonatal Candidemia in developing countries," J Fungi (Basel). 3(3):pii:E41 (2017) (20 pages).
Sherry et al., "Biofilm-forming capability of highly virulent, multidrug-resistant *Candida auris*," Emerg Infect Dis. 23(2):328-331 (2017).
Extended European Search Report for European Patent Application No. 18166876.5, dated Jul. 31, 2018 (10 pages).
Larkin et al., "The Emerging Pathogen Candida auris: Growth Phenotype, Virulence Factors, Activity of Antifungals, and Effect of SCY-078, a Novel Glucan Synthesis Inhibitor, on Growth Morphology and Biofilm Formation," Antimicrob Agents Chemother. 61(5). pii: e02396-16 (2017).
Sui et al., "The vaccines and antibodies associated with Als3p for treatment of Candida albicans infections," Vaccine 35(43):5786-5793 (2017).
Tsay et al., "Approach to the Investigation and Management of Patients With Candida auris, an Emerging Multidrug-Resistant Yeast," Clin Infect Dis. 66(2):306-311 (2018).
Response to Final Office Action filed Nov. 13, 2018 in U.S. Appl. No. 15/014,440 (8 pages).

\* cited by examiner

FIGURE 1A

SEQ ID NO:1

```
   1 MLQQYTLLLI YLSVATAKTI TGVFNSFNSL TWSNAATYNY KGPGTPTWNA VLGWSLDGTS
  61 ASPGDTFTLN MPCVFKFTTS QTSVDLTAHG VKYATCQFQA GEEFMTFSTL TCTVSNTLTP
 121 SIKALGTVTL PLAFNVGGTG SSVDLEDSKC FTAGTNTVTF NDGGKKISIN VDFERSNVDP
 181 KGYLTDSRVI PSLNKVSTLF VAPQCANGYT SGTMGFANTY GDVQIDCSNI HVGITKGLND
 241 WNYPVSSESF SYTKTCSSNG IFITYKNVPA GYRPFVDAYI SATDVNSYTL SYANEYTCAG
 301 GYWQRAPFTL RWTGYRNSDA GSNGIVIVAT TRTVTDSTTA VTTLPFDPNR DKTKTIEILK
 361 PIPTTTITTS YVGVTTSYST KTAPIGETAT VIVDIPYHTT TTVTSKWTGT ITSTTTHTNP
 421 TDSIDTVIVQ VPSPNPTVTT TEYWSQSFAT TTTITGPPGN TDTVLIREPP NHTVTTTEYW
 481 SESYTTTSTF TAPPGGTDSV IIKEPPNPTV TTTEYWSESY TTTSTFTAPP GGTDSVIIKE
 541 PPNHTVTTTE YWSQSYTTTT TVTAPPGGTD TVLVREPPNH TVTTTEYWSQ SYTTTTTVIA
 601 PPGGTDSVII REPPNPTVTT TEYWSQSYAT TTTITAPPGE TDTVLIREPP NHTVTTTEYW
 661 SQSYATTTTI TAPPGETDTV LIREPPNHTV TTTEYWSQSF ATTTTVTAPP GGTDTVIIRE
 721 PPNHTVTTTE YWSQSYATTT TITAPPGETD TVLIREPPNH TVTTTEYWSQ SYATTTTIIA
 781 PPGETDTVLI REPPNPTVTT TEYWSQSYTT ATTVTAPPGG TDTVIIYDTM SSSEISSFSR
 841 PHYTNHTTLW STTWVIETKT ITETSCEGDK GCSWVSVSTR IVTIPNNIET PMVTNTVDST
 901 TTESTSQSPS GIFSESGVSV ETESSTVTTA QTNPSVPTTE SEVVFTTKGN NENGPYESPS
 961 TNVKSSMDEN SEFTTSTAAS TSTDIENETI ATTGSVEASS PIISSSADET TTVTTTAEST
1021 SVIEQPTNNN GGGKAPSATS SPSTTTTANN DSVITGTTST NQSQSQSQYN SDTQQTTLSQ
1081 QMTSSLVSLH MLTTFDGSGS VIQHSTWLCG LITLLSLFI
```

SEQ ID NO:2

```
   1 KTITGVFNSF NSLTWSNAAT YNYKGPGTPT WNAVLGWSLD GTSASPGDTF TLNMPCVFKF
  61 TTSQTSVDLT AHGVKYATCQ FQAGEEFMTF STLTCTVSNT LTPSIKALGT VTLPLAFNVG
 121 GTGSSVDLED SKCFTAGTNT VTFNDGGKKI SINVDFERSN VDPKGYLTDS RVIPSLNKVS
 181 TLFVAPQCAN GYTSGTMGFA NTYGDVQIDC SNIHVGITKG LNDWNYPVSS ESFSYTKTCS
 241 SNGIFITYKN VPAGYRPFVD AYISATDVNS YTLSYANEYT CAGGYWQRAP FTLRWTGYRN
 301 SDAGSNGIVI VATTRTVTDS TTAVTTLPFD PNRDKTKTIE ILKPIPTTTI TTSYVGVTTS
 361 YLTKTAPIGE TATVIVDIPY HTTTTVTSKW TGTITSTTTH TNPTDSIDTV IVQVPL
```

FIGURE 1B

SEQ ID NO:3

```
1     AAGACAATCACTGGTGTTTTCAACAGTTTT AATTCATTGACTTGGTCTAATGCTGCTACG
61    TATAATTATAAGGGACCAGGAACCCCAACT TGGAATGCTGTTTTGGGTTGGTCTTTAGAT
121   GGTACTAGTGCAAGTCCGGGAGATACATTC ACATTGAATATGCCATGTGTGTTTAAATTT
181   ACTACTTCTCAAACATCTGTTGATTTGACT GCTCATGGTGTTAAATATGCTACATGTCAA
241   TTTCAGGCAGGTGAAGAATTTATGACCTTT TCTACATTAACATGTACTGTGAGCAATACT
301   TTGACTCCATCTATTAAGGCTTTGGGTACT GTCACTTTACCACTTGCATTCAATGTAGGT
361   GGAACTGGTTCTTCTGTTGATTTGGAAGAT TCTAAATGTTTTACTGCTGGTACTAACACA
421   GTTACATTTAATGATGGTGGCAAGAAAATC TCAATTAATGTTGATTTTGAAAGGTCAAAT
481   GTCGATCCAAAAGGGTACTTAACTGATTCC AGAGTTATACCAAGTCTCAACAAAGTGTCA
541   ACTCTTTTTGTTGCACCACAATGTGCAAAT GGTTACACATCTGGTACAATGGGATTCGCT
601   AACACTTATGGTGATGTTCAAATTGACTGT TCAAATATTCATGTTGGTATTACAAAAGGA
661   TTGAATGATTGGAATTATCCGGTTTCATCT GAATCATTTAGTTACACCAAAACTTGTTCA
721   TCTAATGGTATCTTTATCACATATAAAAAC GTTCCTGCCGGTTATCGTCCATTTGTTGAC
781   GCTTATATTTCTGCTACAGATGTTAATTCG TACACCTTGTCGTATGCTAATGAATATACT
841   TGTGCTGGTGGTTATTGGCAACGTGCACCT TTCACATTAAGATGGACTGGATACAGAAAT
901   AGTGATGCTGGATCTAACGGTATTGTTATT GTGGCTACTACCAGAACAGTTACAGACAGT
961   ACTACCGCCGTGACCACCTTACCATTCGAT CCTAACCGCGACAAAACTAAGACAATTGAA
1021  ATTTTGAAACCTATTCCAACAACTACAATC ACAACATCATATGTTGGTGTGACTACTTCC
1081  TACCTGACCAAAACTGCACCAATTGGGGAA ACTGCTACTGTTATTGTTGATATTCCATAT
1141  CACACTACCACTACTGTTACCAGTAAATGG ACAGGAACAATTACTTCCACCACAACACAT
1201  ACTAATCCAACTGACTCAATAGACACTGTC ATTGTACAAGTTCCACTGTGA
                                                         *
```

*stop codon

Comparative Efficacy Kinetics of NDV-3 Assessed by *in Vivo* Imaging

NDV-3 Restricts MRSA Abscess Volume in Murine SSSI

Control          100 µg

Mean Abscess Volume (cm$^3$)

NDV-3 Limits MRSA Proliferation and Recruits Neutrophils

Data from 100 μg dose @ 7d post-infection

NDV-3 Recuits CD3+ T Cells and Induces IL-17 Expression

Data from 100 µg dose @ 7d post-infection

NDV-3 Stimulates IL-22 Expression and β-Defensin Response

Data from 100 μg dose @ 7d post-infection

MRSA Abscess from NDV-3 (100 µg) Vaccinated Mouse

MRSA Abscess from Control Mouse

METHODS AND COMPOSITIONS FOR VACCINATING AGAINST *STAPHYLOCOCCUS AUREUS*

CROSS-REFERENCE TO RELATED APPLICATION

This application claims benefit of priority to U.S. Provisional Application No. 61/510,896, filed Jul. 22, 2011, which is hereby incorporated by reference.

STATEMENT AS TO FEDERALLY SPONSORED RESEARCH

This invention was sponsored by the Department of the Army Award No. W81XWH-10-2-0035 awarded by The U.S. Army Medical Research Acquisition Activity, 820 Chandler Street, Fort Detrick Md. 21702-5014 which also serves as administering acquisition office. The content of the information disclosed herein does not necessarily reflect the position or the policy of the Government, and no official endorsement should be inferred. The Government has certain rights in the invention.

BACKGROUND OF THE INVENTION

The invention relates to vaccines against *Staphylococcus aureus*.

*Staphylococcus aureus* is the leading cause of skin and skin structure infections including cellulitis and furunculosis, and is among the most common causes of bacteremia. Strains of *S. aureus* that exhibit the methicillin-resistant (MRSA) phenotype are predominant causes of healthcare- and community-acquired infections, including invasive disease in immune competent hosts, in immune suppression (e.g. neutropenia, solid-organ or bone marrow transplants), and in inherited immune dysfunctions manifesting recurring cutaneous infection (e.g. Job's Syndrome, Chronic Granulomatous Disease). The significant impact of MRSA on public health is of special concern in light of high rates of mortality associated with invasive *S. aureus* disease even with appropriate antimicrobial therapy (e.g. 15-40% in bacteremia and endocarditis). Increasing rates of life-threatening infections and decreasing susceptibility to antibiotics call for development of an effective vaccine targeting *Staphylococcus aureus*. This invention meets this need.

SUMMARY OF THE INVENTION

The invention, in general, relates to a method of vaccinating a mammal against *Staphylococcus aureus* including the steps of: a) identifying a mammal (e.g., a human or non-human mammal, such as livestock, e.g., a bovine, equine, porcine, or ovine species, or a domestic mammal, e.g., a canine or feline) at risk for the development of a *Staphylococcus aureus* skin or soft tissue infection; and b) administering to said mammal an immunogenic amount of a vaccine including a polypeptide comprising an isolated agglutinin-like sequence (Als) 3 protein (Als3p), or an immunogenic fragment thereof, in a pharmaceutically acceptable medium. Exemplary polypeptides include a *Candida albicans* Als3p (for example, an Als3p shown in FIG. 1A, e.g., SEQ ID NO: 1 or SEQ ID NO: 2, or an immunogenic fragment thereof). In other embodiments, the polypeptide includes the N-terminal domain of *Candida albicans* Als3p or an immunogenic fragment thereof. The method disclosed herein is especially useful for vaccination against a methicillin-resistant *Staphylococcus* aureus (MRSA) strain of *S. aureus*. The method disclosed herein is also useful for vaccination against other drug-resistant *S. aureus* (e.g. vancomycin resistant, daptomycin-resistant, etc.), or methicillin-sensitive *S. aureus* (MSSA) strains of *S. aureus*. In other embodiments, the polypeptide is conjugated to a carrier such as a keyhole limpet hemocyanin (KLH), CRM197, tetanus toxoid, diphtheria toxoid, enterotoxin B fragments, *N. meningitides* outer membrane protein complex, or any other carrier protein used in conjugate vaccines in the art. Such carriers also may include a phage, a yeast, a virus, a virosome, or a recombinant virus-like particle. The vaccine, in general, is administered by intramuscular, subcutaneous, intradermal, oral, or sublingual administration, or is administered for inhalation in a microparticulate formulation. If desired, the vaccine is administered as a booster dose. The vaccine optionally may include an immunostimulating adjuvant. In still other embodiments, the method includes administering an antibiotic against *S. aureus* in, combination with the vaccine, e.g., wherein the antibiotic is co-formulated or co-administered with the vaccine.

In another aspect, the invention features a method of vaccinating a mammal (e.g., a human or non-human mammal, such as livestock, e.g., a bovine, equine, porcine, or ovine species, or a domestic mammal, e.g., a canine or feline) against *Staphylococcus aureus* including the steps of: a) identifying a mammal at risk for the development of a *Staphylococcus aureus* skin or soft tissue infection; and b) administering to said mammal an effective amount of a vaccine including a polynucleotide (e.g., an isolated polynucleotide) encoding a polypeptide including an Als3p, or an immunogenic fragment thereof, incorporated into a suitable delivery vehicle, which could include single- or double-stranded DNA or RNA, a double-stranded DNA plasmid or a viral vector, in a pharmaceutically acceptable medium, wherein the polynucleotide is expressed in vivo and the mammal generates an immune response. The vaccine containing the polynucleotide elicits an immune response in the mammal, e.g., the production of anti-Als3p antibodies that exhibit specificities for Als3p.

In yet another aspect, the invention features an isolated Als3 protein, or an immunogenic fragment thereof, for use in a method of treatment or prevention of a *Staphylococcus aureus* skin or soft tissue infection in a mammal.

In another aspect, the invention features a vaccine including an isolated Als3 protein, or an immunogenic fragment thereof, for use in a method of treatment or prevention of a *Staphylococcus aureus* skin or soft tissue infection in a mammal.

Such Als3p useful for preparing isolated proteins or vaccines include those identified in *Candida albicans, Candida krusei, Candida tropicalis, Candida glabrata* and *Candida parapsilosis*, as well as those Alsp3 proteins identified in searches of publically available databases.

In still another aspect, the invention features an isolated Als3 protein, wherein the amino acid sequence of the isolated Als3 protein consists of SEQ ID NO: 2.

In yet another aspect, the invention features a pharmaceutical composition comprising an isolated Als3 protein, wherein the amino acid sequence of the isolated Als3 protein consists of SEQ ID NO: 2, and a pharmaceutically acceptable excipient.

In still another aspect, the invention features a vaccine comprising an isolated Als3 protein, wherein the amino acid sequence of the isolated Als3 protein consists of SEQ ID NO: 2. In some embodiments, the protein is conjugated to a carrier such as a keyhole limpet hemocyanin (KLH), CRM197, tetanus toxoid, diphtheria toxoid, enterotoxin B fragments, *N. meningitides* outer membrane protein complex, or any other carrier protein used in conjugate vaccines in the art. Such carriers also may include a phage, a yeast, a virus, a virosome, or a recombinant virus-like particle. The vaccine, in general, is administered by intramuscular, subcutaneous, intradermal, oral, or sublingual administration, or is administered for inhalation in a microparticulate formulation. If desired, the vaccine is administered as a booster dose. The vaccine optionally may include an immunostimulating adjuvant. In other embodiments, the vaccine may include a combination of an isolated Als3 protein and one or more other isolated Als proteins, e.g., derived from a *Candida* strain selected from the group consisting of *Candida albicans, Candida krusei, Candida tropicalis, Candida glabrata* and *Candida parapsilosis*.

In another aspect, the invention features a vaccine including a polynucleotide (e.g., an isolated polynucleotide) encoding a polypeptide including an Als3p, or an immunogenic fragment thereof, incorporated into a suitable delivery vehicle, which could include single- or double-stranded DNA or RNA, a double-stranded DNA plasmid or a viral vector, in a pharmaceutically acceptable medium. For example, an immunogenic Als3 polynucleotide vaccine, e.g., the nucleic acid sequence of which contains or consists of SEQ ID NO: 3 in part or in its entirety, and which is suitable to be used as a vaccine, may be prepared, e.g., from an Als3 gene or fragment thereof, e.g., a fragment encoding an immunogenic fragment of an Als3p. The vaccine may further include a polynucleotide encoding an immune-stimulant polypeptide that is co-expressed with the Als3p or immunogenic fragment thereof. Such polynucleotide vaccines may be prepared as injectables, e.g., in physiologically-acceptable liquid solutions or emulsions for polynucleotide administration. The polynucleotide may be associated with liposomes, such as lecithin liposomes or other liposomes known in the art, as a nucleic acid liposome (for example, as described in International Application Pub. No. WO 93/24640) or the polynucleotide may be associated with an adjuvant. Liposomes including cationic lipids interact spontaneously and rapidly with polyanions, such as DNA and RNA, resulting in liposome/nucleic acid complexes that capture up to 100% of the polynucleotide. In addition, the polycationic complexes fuse with cell membranes, resulting in an intracellular delivery of polynucleotide that bypasses the degradative enzymes of the lysosomal compartment. International Application Pub. No. WO 94/27435 describes compositions for genetic immunization including cationic lipids and polynucleotides. Agents which assist in the cellular uptake of polynucleotides, such as calcium ions, viral proteins, electroporation and other transfection-facilitating agents, may advantageously be used. Both liquid as well as lyophilized forms that are to be reconstituted include, preferably buffers, in amounts necessary to suitably adjust the pH of the injected solution.

"*Staphylococcus aureus* skin or soft tissue infection", "*Staphylococcus aureus* SSTI", "*Staphylococcus aureus* skin/skin structure infection", and "*Staphylococcus aureus* SSSI" are used interchangeably herein and refer to a skin or soft tissue infection (e.g. cellulitis, soft tissue abscess, dermonecrosis, myositis, or other infections) resulting from *S. aureus* entering the body at a site where a cut, scrape, bite, or other wound has broken the skin. In some instances, *S. aureus* SSSI is the result of *S. aureus* living on the body, and may occur spontaneously in the absence of a visible site of skin injury or wound. Such infections may affect the layers of the skin or deeper tissues, such as muscle and connective tissue (the interlacing framework of tissue that forms ligaments, tendons, and other supporting structures of the body). Skin abscesses may also occur in areas of the skin where the body has been fighting a *S. aureus* infection. The more important strains of *S. aureus* responsible for skin or soft tissue infections are the antibiotic-resistant *Staphylococcus* known as methicillin-resistant *Staphylococcus aureus* (MRSA); vancomycin-resistant and daptomycin-resistant strains of *S. aureus* may also cause SSSI. MRSA is resistant to commonplace antibiotics. *Staphylococcus aureus* SSSIs may also be caused by methicillin-sensitive *Staphylococcus aureus* (MSSA).

Mammals which are at risk of developing a *S. aureus* skin or soft tissue infection can be treated in a prophylactic mode. Alternatively, mammals may be treated when presenting with symptoms of a *S. aureus* skin or soft tissue infection. Vaccination as described herein will reduce the severity, delay, or prevent the development of symptoms. Mammals are at elevated risk of infection if they are hospitalized or living in an institutionalized community, antibiotic treated, or immunosuppressed including children having HIV/AIDS or other diseases that compromise immune function, individuals having frequent contact with the healthcare system, having a chronic illness such as diabetes, cancer, HIV/AIDS, being very young or very old, frequent use of antibiotics, having an open wound, dermatitis or skin lesions, poor nutrition or poor hygiene. Other mammals at risk include those living in crowded living conditions, military personnel, especially deployed troops, athletes, and prison inmates. Still others at risk of developing a *S. aureus* skin or soft tissue infection are those individuals previously having such infections or individuals scheduled for or having had a surgical or invasive medical procedure.

By "Als3p" is meant a polypeptide that is substantially identical to the amino acid sequence of a sequence shown in FIG. 1A, e.g., SEQ ID NO: 1 or SEQ ID NO: 2, or to a *Candida* ALS3 protein identified in GenBank: XP_710431.1, XP_710435.1, AAO72959.1, XP_712646.1, XP_712666.1, EAK91173.1, EAK91169.1, AAO72958.1, EAK93494.1, EAK93472.1, O74623.1, AAD02580.1, EAK90704.1, XP_709985.1. Desirably, a Als3p has at least 70, 75%, 80%, 85%, 90%, 95%, 99%, or even 100% identity to a sequence shown in FIG. 1A, e.g., SEQ ID NO: 1 or SEQ ID NO: 2.

By "Als3p fragment" or "fragment of a Als3p" is meant a portion of a Als3p polypeptide containing fewer than 1050, 1025, 1000, 975, 950, or 945 amino acids. In some embodiments, Als3p fragments are between 300 and 350 or 250 to 500 amino acids in length. In some embodiments, the fragment is fewer than 1050, 1025, 1000, 975, 950, or 945, 940, 937, 936, 935, 934, 933, 932, 931, or 930, 920, 910, 900, 890, 880, 870, 860, 850, 840, 830, 820, 810, 800, 790, 780, 770, 760, 750, 740, 730, 720, 710, 700, 690, 680, 670, 660, 650, 640, 630, 620, 610, 600, 590, 580, 570, 560, 550, 540, 530, 520, 510, 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 30, 25, 20, 15, or 10 amino acids, and, in some instances, is immunogenic.

An exemplary Als3p fragment is SEQ ID NO: 2, as shown in FIG. 1A, or fragments thereof. In some instances, Als3p fragments are between 14 and 20 amino acids in length. In general, the fragment may be fewer than, e.g., 325, 320, 310, 300, 290, 280, 270, 260, 250, 240, 230, 220, 210, 200, 190, 180, 170, 160, 150, 140, 130, 120, 110, 100, 90, 80, 70, 60, 50, 40, 30, 25, 20, 19, 18, 17, 16, 15, 14, 13, 12, or 11 amino acids, and desirably, is immunogenic. In some instances, an Als3p fragment is between 14 and 20 amino acids.

In addition, Als3p fragments, for example, may contain one or more conservative amino acid substitutions in a sequence shown in FIG. 1A, e.g., SEQ ID NO: 1 or SEQ ID NO: 2. Additional desirable Als3p fragments contain one or more conservative amino acid substitutions in a sequence shown in FIG. 1A, e.g., SEQ ID NO: 1 or SEQ ID NO: 2, and/or at least one flanking amino acid (e.g., 1, 2, 3, 4, 5, 6, 7, 8, 9, or 10 flanking amino acids) at the N- and/or C-terminus of a sequence shown in FIG. 1A, e.g., SEQ ID NO: 1 or SEQ ID NO: 2. Other preferred Als3p fragments contain seven or more continuous amino acids of a sequence shown in FIG. 1A, e.g., SEQ ID NO: 1 or SEQ ID NO: 2.

Non-limiting examples of an Als3p fragment include amino acids 1-40, 10-50, 20-60, 30-70, 40-80, 50-90, 60-100, 70-110, 80-120, 90-130, 100-140, 110-150, 120-160, 130-170, 140-180, 150-190, 160-200, 170-210, 180-220, 190-230, 200-240, 210-250, 220-260, 230-270, 240-280, 250-290, and 260-300, 270-310, 280-320, and 290-331 amino acids of a sequence shown in FIG. 1A, e.g., SEQ ID NO: 1 or SEQ ID NO: 2; and these fragments having one or more of the following features: one or more conservative amino acid substitutions (e.g., 1, 2, 3, 4, 5, 6, 7, 8, 9, 10, 11, 12, 13, 14, 15, or 16 conservative amino acid substitutions) in a sequence shown in FIG. 1A, e.g., SEQ ID NO: 1 or SEQ ID NO: 2; one or more amino acids (e.g., 1, 2, 3, 4, 5, 6, 7, 8, 9, 10, 11, 12, 13, 14, 15, or 16 amino acids) truncated from the N and/or C-terminus of a sequence shown in FIG. 1A, e.g., SEQ ID NO: 1 or SEQ ID NO: 2; and at least one flanking amino acid (e.g., 1, 2, 3, 4, 5, 6, 7, 8, 9, or 10 flanking amino acids) at the N- and/or C-terminus of a sequence shown in FIG. 1A, e.g., SEQ ID NO: 1 or SEQ ID NO: 2.

By "substantially identical" is meant an amino acid sequence or nucleic acid sequence that exhibits at least 50% identity to a reference sequence. Such a sequence is generally at least, e.g., 50%, 60%, 70%, 75%, 80%, 85%, 90%, 95%, 96%, 97%, 98%, or 99% identical at the amino acid level or nucleic acid level to a reference sequence. In general, for polypeptides, the length of comparison sequences can be at least five amino acids, e.g., 10, 20, 30, 40, 50, 60, 70, 80, 90, 100, 125, 150, 175, 200, 250, 300, or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, or more nucleotides, up to the entire length of the nucleic acid molecule. It is understood that for the purposes of determining sequence identity when comparing a DNA sequence to an RNA sequence, a thymine nucleotide is equivalent to a uracil nucleotide.

Also contemplated are nucleic acid sequences that encode any of the Als3p polypeptides or fragments thereof recited herein.

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith et al., J. Mol. Biol. 147:195-7, 1981) and BLAST (Basic Local Alignment Search Tool; Altschul et al., J. Mol. Biol. 215: 403-10, 1990). These and other alignment algorithms are accessible using publicly available computer software such as "Best Fit" (Smith and Waterman, Advances in Applied Mathematics, 482-489, 1981) as incorporated into GeneMatcher Plus™ (Schwarz and Dayhof, Atlas of Protein Sequence and Structure, Dayhoff, M. O., Ed pp 353-358, 1979), BLAST, BLAST-2, BLAST-P, BLAST-N, BLAST-X, WU-BLAST-2, ALIGN, ALIGN-2, CLUSTAL, or Megalign (DNASTAR). In addition, those skilled in the art can determine appropriate parameters for measuring alignment, including any algorithms needed to achieve optimal alignment over the length of the sequences being compared.

By "adjuvant" is meant one or more substances that cause stimulation of the immune system. In this context, an adjuvant is used to enhance an immune response to one or more vaccine antigens or antibodies. An adjuvant may be administered to a subject before, in combination with, or after administration of the vaccine or antibody. Examples of chemical compounds used as adjuvants include, but are not limited to, aluminum compounds (e.g., alum, Alhydrogel), oils, block polymers, immune stimulating complexes, vitamins and minerals (e.g., vitamin E, vitamin A, selenium, and vitamin B12), Quil A (saponins), bacterial and fungal cell wall components (e.g., lipopolysaccarides, lipoproteins, and glycoproteins), hormones, cytokines, and co-stimulatory factors.

By "carrier" in the context of a conjugate is meant a moiety or particle, e.g., KLH, CRM197, tetanus toxoid, diphtheria toxoid, enterotoxin B fragments, *N. meningitides* outer membrane protein complex, any other carrier protein, a phage, a yeast, a virus, a virosome, or a recombinant virus-like particle, that is suitable for being linked to or displaying a polypeptide as described herein.

By "conjugate" is meant a compound that includes a polypeptide of the invention linked to another moiety or particle, e.g., KLH, CRM197, tetanus toxoid, diphtheria toxoid, enterotoxin B fragments, *N. meningitides* outer membrane protein complex, any other carrier protein, a phage, a yeast, a virus, a virosome, or a recombinant virus-like particle.

By "immunogenic" is meant any substance that is capable of inducing an immune response in a subject.

By "immunogenic amount" in the context of a vaccine is meant an amount of the vaccine required to induce an immune response in a subject in a clinically relevant manner. An immunogenic amount of vaccine used to practice the methods of vaccination as described herein varies depending upon the manner of administration, the age, body weight, and general health of the subject. Ultimately, prescribers will decide the appropriate amount and dosage regimen.

By "isolated" or "purified" is meant separated from other naturally accompanying components. Typically, a compound (e.g., nucleic acid, polypeptide, antibody, or small molecule) is substantially isolated when it is at least 60%, by weight, free from the proteins and/or naturally occurring organic molecules with which it is naturally associated. The definition also extends, e.g., to a polypeptide or nucleic acid molecule separated from its flanking sequences (e.g., for an amino acid sequence, isolated refers to a sequence that is free from the flanking amino acids with which the sequence is naturally associated in a polypeptide). In some instances, the compound is at least 75%, more preferably at least 90%, and most preferably at least 99%, by weight, isolated. An isolated compound, e.g., polypeptide, may be obtained by standard techniques, for example, by extraction from a natural source (e.g., purification from a cell infected with *Candida*); by expression of a recombinant nucleic acid encoding an Als3p, an Als3p fragment or variant, or a fusion protein thereof in any standard expression system including but not limited to E. coli or Saccharomyces cerevisiae; or by chemically synthesizing the polypeptide. Purity can be measured by any appropriate method, e.g., by column chromatography, polyacrylamide gel electrophoresis, or HPLC analysis.

By "linked to" or "conjugated to" in the context of a conjugate is meant a covalent or non-covalent interaction between the polypeptide and the carrier or fusion partner. Non-covalent interactions include, but are not limited to, hydrogen bonding, ionic interactions among charged groups, electrostatic binding, van der Waals interactions, hydrophobic interactions among non-polar groups, lipophobic interactions, and Log P-based attractions.

The terms "peptide," "polypeptide," and "protein" are used interchangeably and refer to any chain of two or more natural or unnatural amino acids, regardless of post-translational modification (e.g., glycosylation or phosphorylation), constituting all or part of a naturally-occurring or non-naturally occurring polypeptide or peptide, as is described herein.

The terms "pharmaceutically acceptable carrier" and "pharmaceutically acceptable excipient" are used interchangeably and mean a carrier or excipient that is physiologically acceptable to the treated mammal while retaining the therapeutic properties of the compound with which it is administered. One exemplary pharmaceutically acceptable carrier substance is physiological saline. Other physiologically acceptable carriers and their formulations are known to those skilled in the art and described, for example, in Remington's Pharmaceutical Sciences, (21$^{th}$ edition), ed. A. Gennaro, 2005, Lippincott, Williams & Wilkins, Philadelphia, Pa.

By "pharmaceutical composition" is meant a composition containing a polypeptide, conjugate, vaccine, or antibody of the invention, formulated with a pharmaceutically acceptable excipient, and manufactured or sold with the approval of a governmental regulatory agency as part of a therapeutic regimen for the treatment or prevention of a disease or event in a mammal. Pharmaceutical compositions can be formulated, for example, for intravenous administration (e.g., as a sterile solution free of particulate emboli and in a solvent system suitable for intravenous use), for oral administration (e.g., a tablet, capsule, caplet, gelcap, or syrup), or any other formulation described herein, e.g., in unit dosage form.

By "treating" or "treatment" is meant the medical management of a mammal, e.g., a human or non-human mammal, with the intent to cure, ameliorate, stabilize, reduce the likelihood of, or prevent a disease, pathological condition, disorder, or event, by administering a pharmaceutical composition. This term includes active treatment, that is, treatment directed specifically toward the improvement or associated with the cure of a disease, pathological condition, disorder, or event, and also includes causal treatment, that is, treatment directed toward removal of the cause of the associated disease, pathological condition, disorder, or event. In addition, this term includes palliative treatment, that is, treatment designed for the relief of symptoms rather than the curing of the disease, pathological condition, disorder, or event; symptomatic treatment, that is, treatment directed toward constitutional symptoms of the associated disease, pathological condition, disorder, or event; preventative treatment, that is, treatment directed to minimizing or partially or completely inhibiting the development of the associated disease, pathological condition, disorder, or event, e.g., in a mammal who is not yet ill, but who is susceptible to, or otherwise at risk of, a particular disease, pathological condition, disorder, or event; and supportive treatment, that is, treatment employed to supplement another specific therapy directed toward the improvement of the associated disease, pathological condition, disorder, or event.

By "vaccine," as used herein, is meant a composition that elicits an immune response in a subject to which it is administered. The mode of administration, dose, and number of administrations can be optimized by those skilled in the art in a known manner.

By "vaccinate" or "vaccinating" as used herein, is meant to treat a mammal by administering a vaccine, e.g., to prevent or ameliorate a disease, pathological condition, disorder, or event.

Other features and advantages of the invention will be apparent from the following Detailed Description, the drawings, and the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A is a listing of two Als3p amino acid sequences, SEQ ID NO: 1 and SEQ ID NO: 2.

FIG. 1B is a listing of one Als3 nucleic acid sequence, SEQ ID NO: 3.

DETAILED DESCRIPTION

Figure 2:
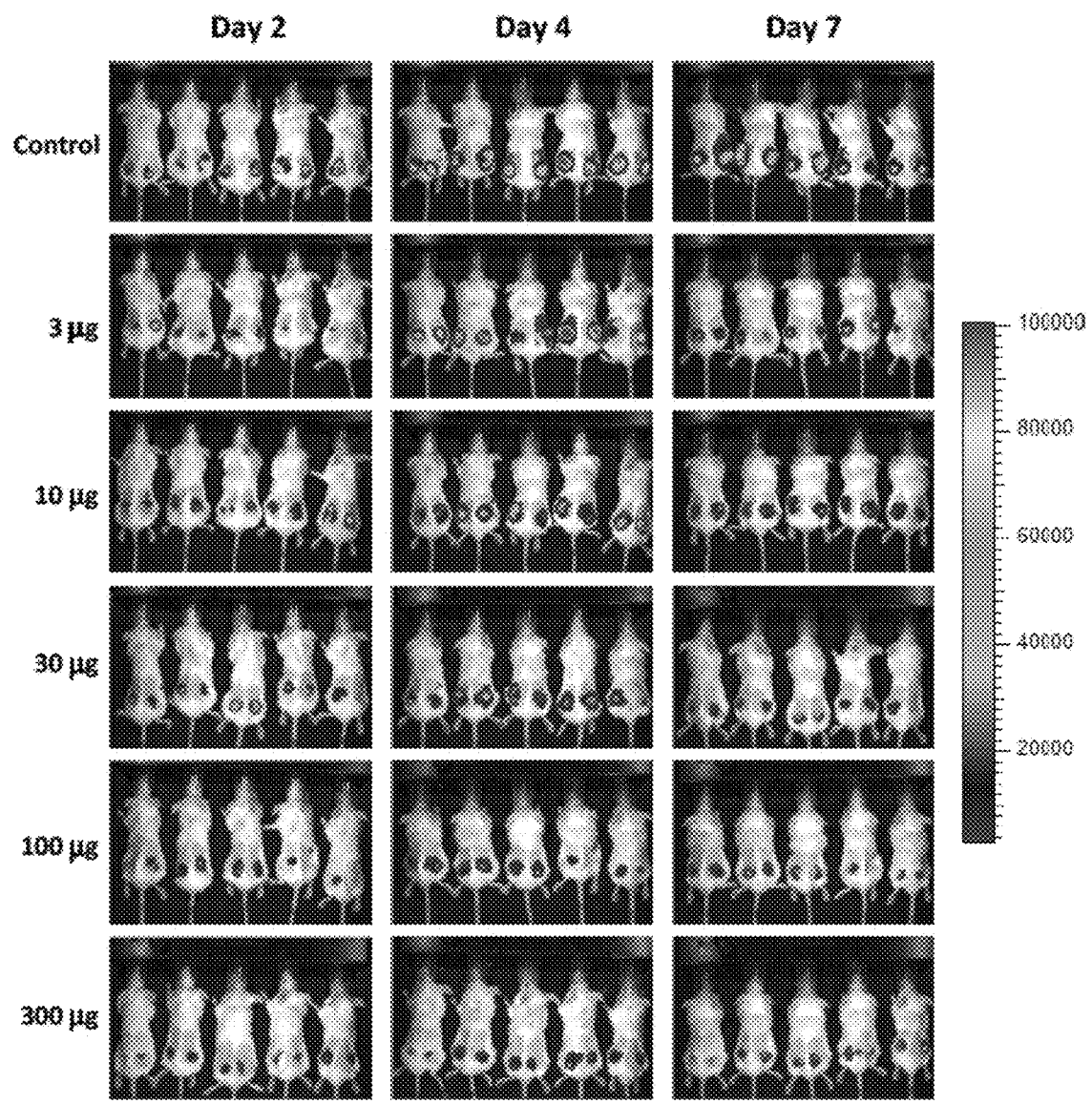
FIG. 2 is a set of photographs showing comparative efficacy kinetics of NDV-3 assessed by in vivo imaging. The photographs show mice in each of the dosage groups at days 2, 4, and 7 post-infection.
Figure 3:
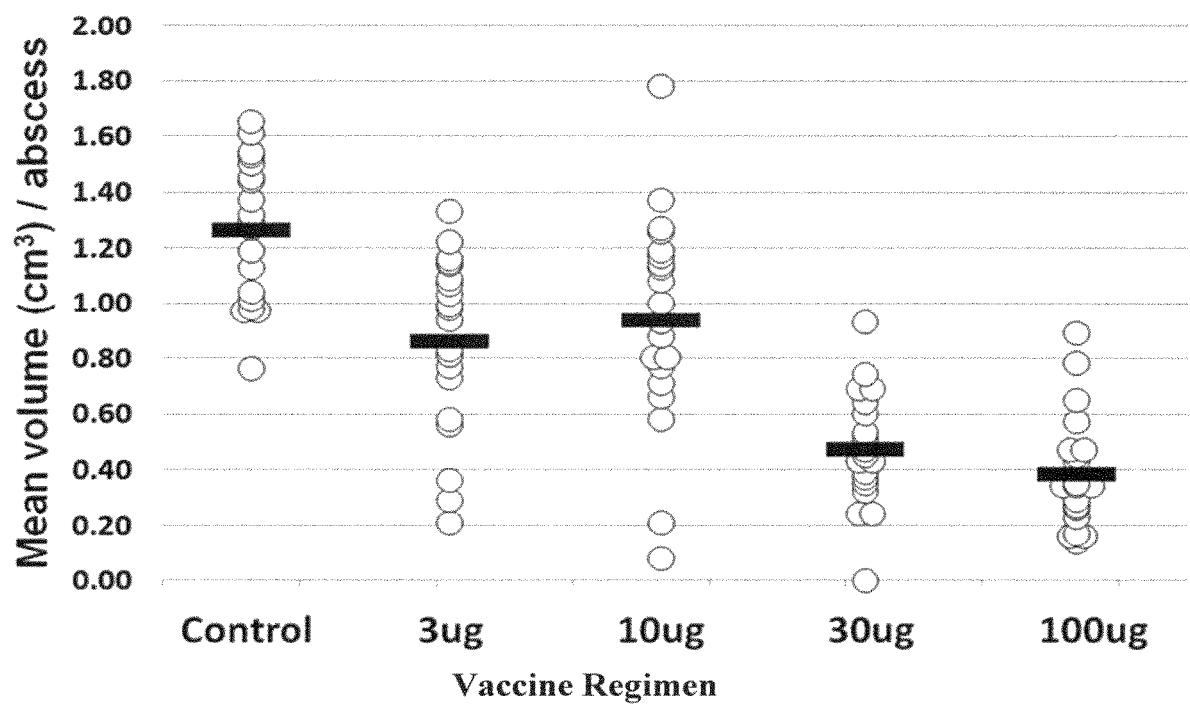
FIG. 3 is a chart showing that NDV-3 restricts MRSA abscess volume in murine SSSI. The chart shows mean volume (cm3)/abscesses for the control group and the 3 µg, 10 µg, 30 µg, and 100 µg NDV-3 dosage groups.
Figure 4:
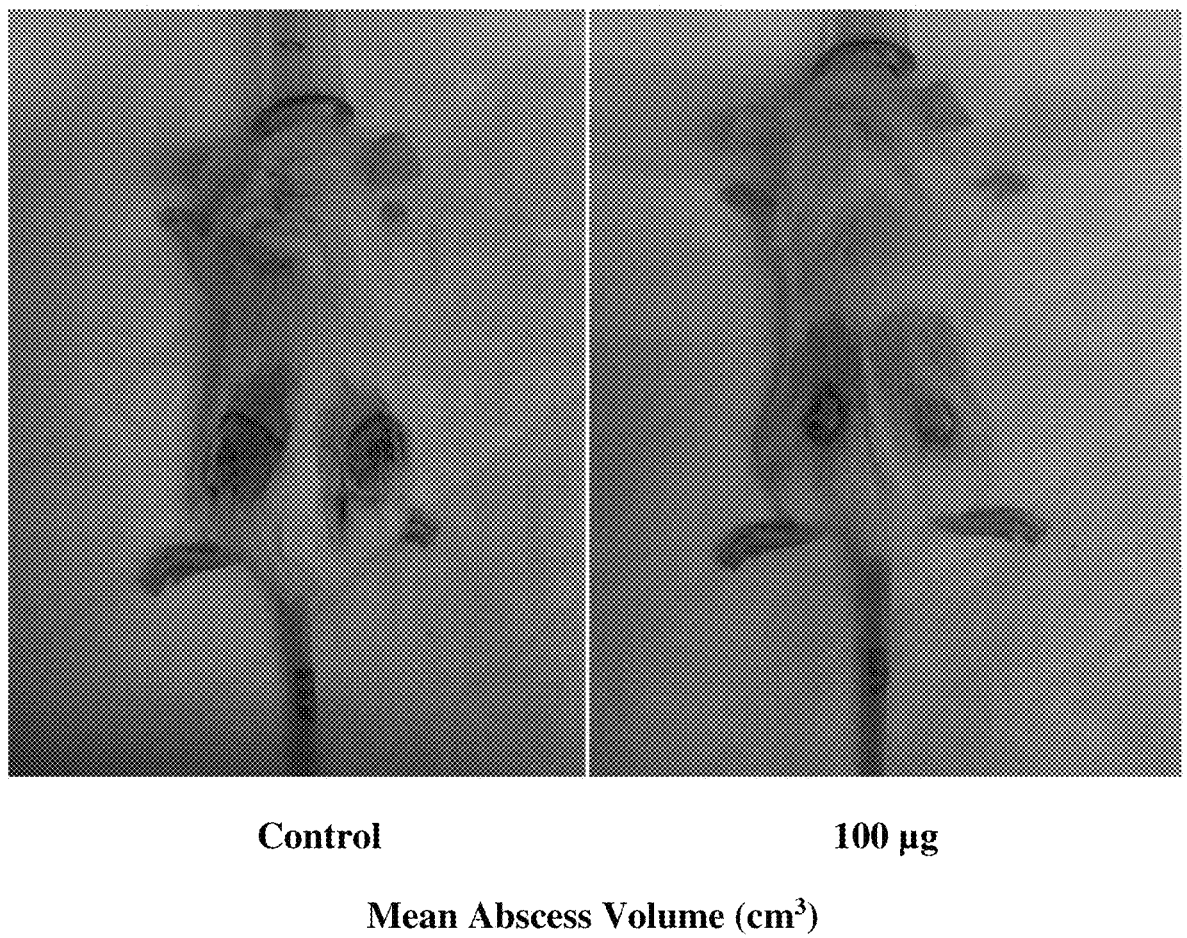
FIG. 4 is a pair of photographs showing that NDV-3 restricts MRSA abscess volume in murine SSSI. Left, mouse in control group; right, mouse in 100 µg NDV-3 dosage group.
Figure 5:
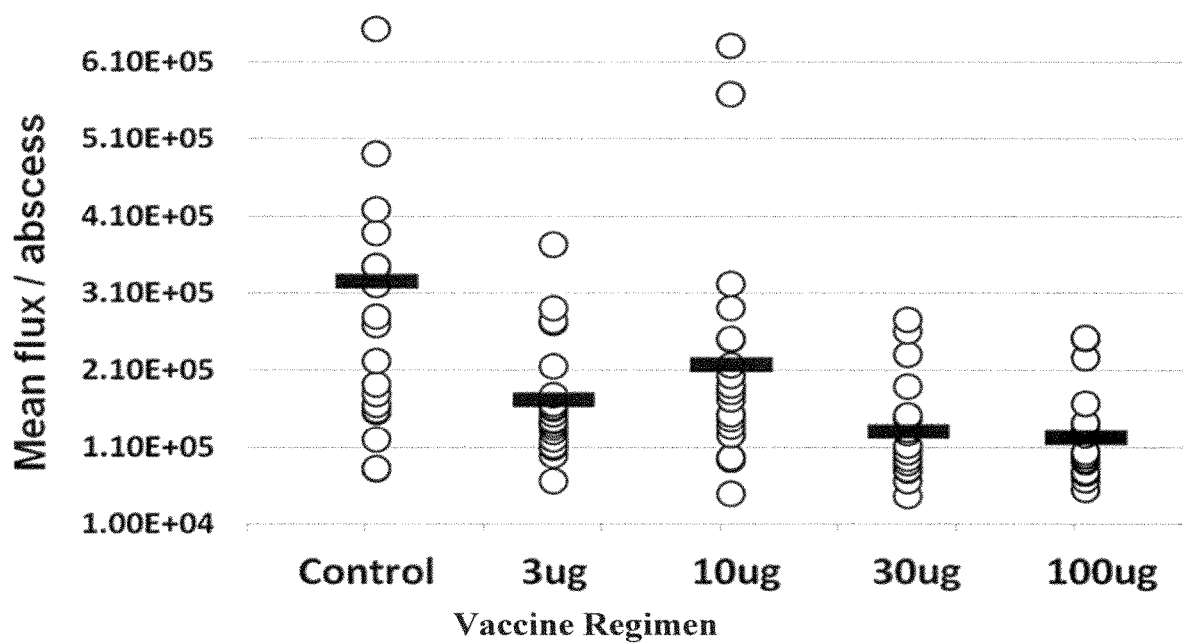
FIG. 5 is a chart showing that NDV-3 suppresses MRSA proliferation in murine SSSI. The chart shows mean flux/ abscess for the control group and the 3 µg, 10 µg, 30 µg, and 100 µg NDV-3 dosage groups.
Figure 6:
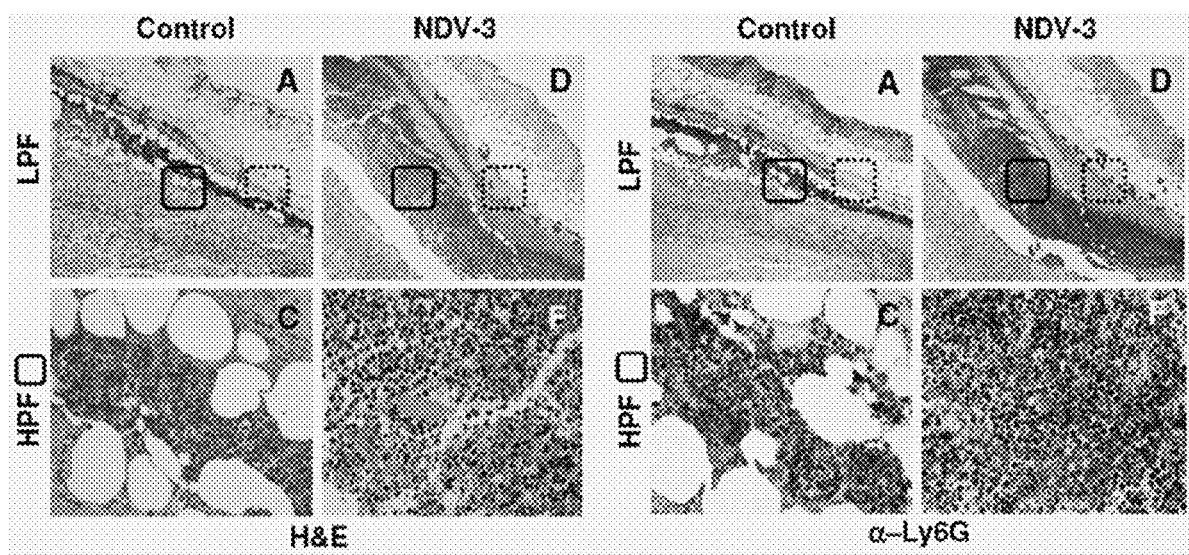
FIG. 6 is a set of images showing that NDV-3 limits MRSA proliferation and recruits neutrophils. The data shown are from the 100 µg NDV-3 dosage group at day 7 post-infection.
Figure 7:
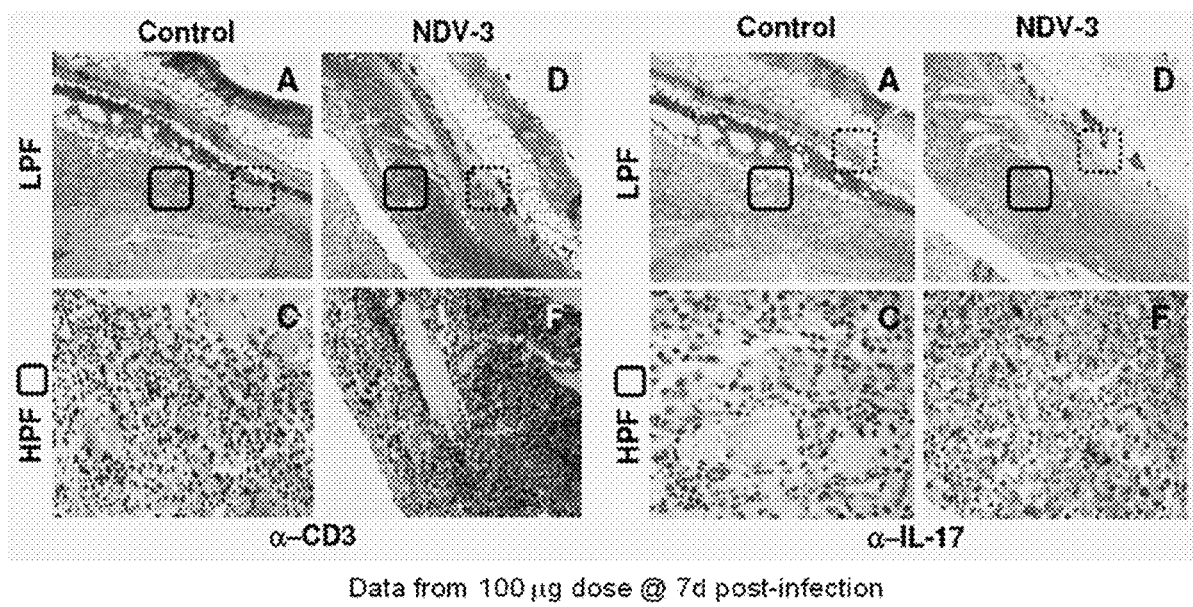
FIG. 7 is a set of images showing that NDV-3 recruits CD3+ T cells and induces IL-17 expression. The data shown are from the 100 µg NDV-3 dosage group at day 7 post-infection.
Figure 8:
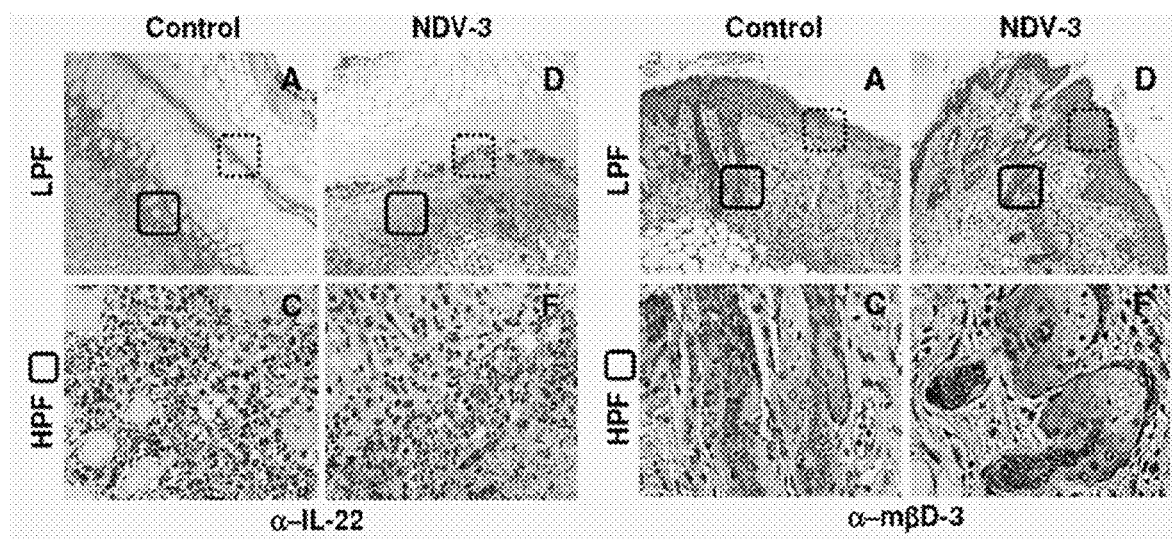
FIG. 8 is a set of images showing that NDV-3 stimulates IL-22 expression and β-defensin response. The data shown are from the 100 µg NDV-3 dosage group at day 7 post-infection.

As is described below, agglutinin-like sequence 3 protein (Als3p) allows for vaccination against S. aureus in mammals identified as being at risk for development of an S. aureus skin or soft tissue infection.

In the following analyses (in particular, the pilot study of Example 1 and the optimized study of Example 2) designed to evaluate the efficacy of an Als3p vaccine against the development of skin or soft tissue infection resulting from S. aureus in a murine model of MRSA skin/skin structure infection (SSSI), the organisms and methods are first described.

Organisms

MRSA Strains

MRSA Xen30 (lux+) Roche-16
MRSA LAC-USA300 USA300
MRSA MW2 USA400

*Staphylococcus aureus* strain Xen30 was used in these in vivo studies. It is derived from the parental strain *S. aureus* MRSA-16 (Roche) and contains a luxA-E operon at a single chromosomal integration site. This MRSA strain produces luciferase enzyme and aldehyde substrate, and constitutively emits a bioluminescent signal when metabolically active. Its virulence is equivalent to other MRSA strains in the SSSI murine model used as verified in pilot studies, and all strains tested have otherwise similar phenotypes and growth characteristics. Log-phase cells (BHI; 37° C.) were cultured from quantitatively- and virulence-validated master cell banks, harvested and suspended in PBS, sonicated and quantified by spectrophotometry to desired CFU.

Methods

NDV-3 vaccine efficacy was evaluated in a murine SSSI model vs. methicillin-resistant SA (MRSA): Xen30 (lux+); LACUSA300; or MW2 (USA400). NDV-3 is a formulation of the recombinant N-terminus of the *Candida* surface protein Als3 protein (FIG. 1A; SEQ ID NO:2) and the adjuvant Alhydrogel®, in phosphate-buffered saline, pH 7, e.g., with a 0.5 mL dose containing, e.g., 30-300 µg Als3 protein, and optionally further containing aluminum hydroxide at 1.0 mg Al/mL. Efficacy was compared among NDV-3 regimens administered with alhydrogel adjuvant (IM) on day 0 and boosted on day 21. Controls received adjuvant alone. Infection by subcutaneous inoculation of two flanks ($2\times10^7$ CFU) occurred 14 days after boost. Abscess area, volume, and CFU were quantified for multiple days post-challenge. In vivo imaging (IVIS) of abscess flux was done in mice infected by Xen30. Serum IgG (ELISA), IFN-γ and IL-17A (ELISpot) responses were quantified in parallel vaccine regimens. Tissue IL-17A, IL-22, mβD-3, CD3+ cell and neutrophil signals were assessed on day 7 post-infection by immunohistochemistry.

Vaccine.

The NDV-3 vaccination was evaluated across a dose range using an identical regimen of alhydrogel adjuvant. Doses of 3, 10, 30, 100, or 300 µg (IM) were studied in parallel. Primary vaccination (day 0) was followed by an identical boost on study day 21. Mice were infected 14 days after boost (study day 35).

Murine Model of SSSI.

All animal studies were performed per the approved animal use policies of LABioMed at Harbor-UCLA. Balb/C mice (Harlan) were vaccinated as above. A subcutaneous skin/soft tissue abscess model was modified from Ding et al. (*J Bacteriol* 2008 190:7123-9) and/or Voyich et al. (*J Infect Dis* 2006 194:1761-1770) for these studies. On study day 35, mice were anesthesized, flanks were shaved and sterilized, and $2\times10^7$ CFU inocula (without beads or matrix) were introduced into the subcutaneous compartment by injection (100 µl). A minimum of 20 mice per control or vaccine-regimen groups were used in each study.

Abscess Quantification.

Abscess area/volume were measured in each mouse flank during the study period up to 14 days post-challenge. To do so, mice were anesthetized, and the lesion site length (l) and width (w) assessed to quantify abscess or dermonecrosis area ($cm^2$). Abscess volume ($cm^3$) was calculated per the formula for a spherical ellipsoid: $[v=(\pi/6)\times l\times w^2]$.

Imaging Studies.

The Xen30 MRSA strain has a self-contained lux operon integrated in its chromosome. The construct encodes the aldehyde substrate and the luciferase enzyme itself; thus, no exogenous luciferin substrate is required (Kadurugamuwa et al., *Infect Immun* 2003 71:882-890). On selected study days, control and vaccinated mice underwent in vivo imaging (IVIS) using an IVIS system (Caliper Life Sciences, Inc.). Luminescence signals were captured over a five-minute time period and analyzed using the Living Image software as photons/min/abscess.

Quantitative Culture.

At pre-selected times post-infection, mice were humanely sacrificed and processed for quantitative culture of abscesses. Each flank was aseptically dissected, the abscess removed and prepared for culture. Abscesses were individually homogenized, and serially diluted in sterile PBS for quantitative culture onto sheep blood agar plates. Cultures were incubated (37° C.) for 24 hours, and resulting colonies enumerated.

Immunological Mechanisms.

Multiple and complementary approaches were used to assess potential correlates of NDV-3 vaccine efficacy in the murine model of SSSI due to MRSA. These studies focused on strain Xen30, allowing correlation with IVIS data at the 7d endpoint.

A. Antibody Quantification.

Serum IgG antibody levels were determined in a 96-well ELISA format over a range dilutions. Values represent geometric mean corrected dilution of triplicate assays comparing immunized vs. control sera.

B. Cytokine Quantification.

T cell IFN-γ and IL-17A responses were determined by ELISpot analysis of splenocytes isolated from immunized vs. control mice, and exposed to the NDV-3 immunogen. The number of spot-forming units (SPUs or SFUs, used interchangeably) was quantified per $10^6$ cells producing either IFN-γ or IL-17A. Cell viability was verified by production of IFN-γ following stimulation with phorbol-12-myristate-13-acetate (PMA) and ionomycin per established protocols.

C. Immunohistochemistry.

Immunological determinants associated with vaccine efficacy were assessed in tissues obtained from vaccinated and control animals after 7d of infection by standard methods. For immunohistochemical studies, in brief 3 µm vertical paraffin embedded sections were de-waxed and rehydrated followed by heat-induced antigen retrieval in target retrieval solution (Dako, Carpinteria, Calif.). Sections were incubated with dual endogenous blocking buffer (Dako) for 15 min at room temperature to block endogenous peroxidase activity, and non-specific antibody binding was blocked by incubation with 5% normal serum corresponding to the primary antibody. Sections were then incubated overnight at 4° C.

with a primary antibody targeting a specific antigen of interest (Table 1). Sections were then washed and incubated for 30 min with an appropriate secondary antibody (Table 1), either horseradish peroxidase (HRP)-conjugated or biotinylated (Santa Cruz Biotechnology, Santa Cruz Calif.). Immunohistochemical development was then achieved by 30 min development with streptavidin-HRP (Dako) and 3,3'-diaminobenzidine (DAB; Vector Laboratories, Burlingame, Calif.), and counterstained with hematoxylin. Images were visualized using an Olympus BX43 microscope employing a DP21 digital camera for image capture.

D. Immunofluorescence.

To evaluate the impact of NDV-3 vaccination on the interrelationships of immunologic determinants and *S. aureus* in context of infection in vivo, immunofluorescence studies employing confocal microscopy were performed using established methods. In brief, paraffin embedded sections were prepared as above and incubated with immunofluorescence buffer (1% bovine serum albumin and 2% fetal calf serum) for one hour at room temperature. Primary antibodies directed at target antigens of interest (Table 1) were incubated with tissue sections from control or vaccinated mice at 4° C. overnight. Next, corresponding secondary antibodies (Table 1) diluted in IFF buffer (2 μg/ml) were incubated for 60 minutes. Sections were then washed in PBS, and mounted using Vectashield H-1500 (Vector Laboratories, Burlingame, Calif.) to minimize photobleaching. Images were visualized using a Leica SP2 confocal microscope employing argon (488 nm), krypton (568 nm) and helium-neon (633 nm) lasers and confocal version 2.0 software (Leica Instruments, Germany).

TABLE 1

Antibodies used for immunohistochemical or immunofluorescence studies.

Primary antibodies
Target Antigen

Ly-6G (granulocytes)
Ly-6C (monocytes/macrophages)
Mouse β-defensin-1 (mBD-1)
Mouse β-defensin-3 (mBD-3)
Mouse platelet factor 4 (PF-4)
*Staphylococcus aureus* (mouse)
*Staphylococcus aureus* (rabbit)
Staphylococcal protein A
CD3-γ
CD3-ε
IL-17
IL-22
Secondary Antibodies ALEXA FLUOR® 488-conjugated donkey α-rabbit
ALEXA FLUOR® 488-conjugated donkey α-rat
ALEXA FLUOR® 555-conjugated goat α-rat
ALEXA FLUOR® 568-conjugated donkey α-rabbit
ALEXA FLUOR® 633-conjugated donkey α-goat
ALEXA FLUOR® 647-conjugated donkey α-rabbit
ALEXA FLUOR® 633-conjugated streptavidin Statistical Analyses.

Differences in experimental results were compared based on power estimates indicating that 16-20 mice per group yields >85% power to detect 1 log difference in CFU per gram tissue, or 2 mm abscess area (a=0.05; Mann-Whitney U test. P values are defined in Table 2 and Table 3 (below).

Example 1

In a pilot study, vaccination with NDV-3 reduced SSSI parameters due to MRSA, with equivalent efficacy in limiting abscess area, volume, and CFU for strains Xen30, USA300, and MW2. Murine immune response correlated with NDV-3 dose-related protective efficacy. These results are shown in Table 2 and FIG. 2. These results indicate the NDV-3 vaccine induced robust B and T cell responses which correspond with protective efficacy against MRSA in the murine model of SSSI.

TABLE 2

NDV-3 Efficacy in MRSA Xen30 SSSI and Immune Response in Murine Models.

| Abscess | Control | 3 μg | 10 μg | 30 μg | 100 μg | 300 μg |
|---|---|---|---|---|---|---|
| Area 7 d | 1.88 cm$^2$ | 1.47 cm$^{2*}$ | 1.59 cm$^{2*}$ | 0.99 cm$^{2\dagger\dagger}$ | 0.77 cm$^{2\dagger\dagger}$ | 0.69 cm$^{2\dagger\dagger}$ |
| Volume 7 d | 1.29 cm$^3$ | 0.95 cm$^{3*}$ | 0.96 cm$^{3**}$ | 0.46 cm$^{3\dagger\dagger}$ | 0.34 cm$^{3\dagger\dagger}$ | 0.29 cm$^{3\dagger\dagger}$ |
| Flux 7 d | 1.92 × 10$^5$ | 1.48 × 10$^{5*}$ | 1.81 × 10$^5$ | 1.07 × 10$^{5*}$ | 1.65 × 10$^{5*}$ | 9.03 × 10$^{4\dagger\dagger}$ |
| Median Log CFU 7 d IM | 7.9 (7.6/8.0) [n = 36] | 7.8 (7.8/7.8) [n = 20] | 8.1 (7.8/7.8) [n = 20] | 8.1 (7.9/7.9) [n = 36] | 7.9 (7.5/8.0) [n = 36] | 7.5$^\dagger$ (7.4/7.8) [n = 36] |
| Median Log CFU 14 d IM | 1.70 (1.0/2.8) [n = 48] | 0.05$^{\Delta\dagger\dagger}$ (0.05/1.3) [n = 39] | ND | ND | 0.05$^{\Delta\dagger\dagger}$ (0.05/1.7) [n = 39] | 1.48 (0.05/2.6) [n = 17] |
| Median Log CFU 14 d SubQ | 3.54 (2.6/6.9) [n = 20] | 3.92 (3.2/5.5) [n = 20] | ND | ND | 2.26** (1.8/3.6) [n = 20] | 2.40** (1.4/3.8) [n = 20] |
| Analyte | | | | | | |
| IgG | 1.0 GCU | 44.8 GCU$^{\dagger\dagger}$ | ND | 97.8 GCU$^{\dagger\dagger}$ | 81.8 GCU$^{\dagger\dagger}$ | ND |
| IFN-γ | 9.5 SPU | 12.8 SPU | ND | 21.9 SPU | 34.3 SPU* | ND |
| IL-17 | 18.9 SPU | 132.6 SPU$^{\dagger\dagger}$ | ND | 62.2 SPU | 161.2 SPU** | ND |

(25%/75% quartiles);
*P < 0.5;
**P < 0.1;
$^\dagger$P < 0.05;
$^{\dagger\dagger}$P < 0.01;
GCU, geomean/dilution corrected units;
SPU, mean spot forming units/10$^6$ splenocytes;
$^\Delta$limit of detection.

Analysis

The NDV-3 vaccine significantly reduced the abscess area, volume, luminescence signal, and CFU densities in this murine model of MRSA SSSI. NDV-3 efficacy was equivalent for each of the MRSA strains evaluated in this study. Immunological data from mice vaccinated identically to those challenged with infection indicate the NDV-3 vaccine induces robust B and T cell responses which appear to reflect a dose-response relationship. Immunological data from mice vaccinated identically to those challenged with infection indicate the NDV-3 vaccine induces robust B and T cell responses which reflect a dose-response relationship. Collectively these results provide evidence that NDV-3 induces a mixed Th1/Th17 response that appears to be predominantly associated with protective efficacy. Antibody response may contribute to protective mechanisms of NDV-3. These results indicate that the NDV-3 vaccine is useful as a means to prevent or mitigate MRSA skin infection or abscesses or both in mammals.

Example 2

A further, optimized analysis was conducted, and results are summarized in Table 3 and FIGS. 3-8. Like Example 1, this study evaluated the efficacy and immunologic mechanisms of the NDV-3 vaccine in a murine model of skin/skin structure infection due to methicillin-resistant SA (MRSA). Abscess size, MRSA density and CFU were compared over time in NDV-3 immunized and control groups. Serum concentrations of IgG, IFNγ, IL-17A, induction of tissue IL-17A, IL-22, and mβD-3, and infiltration of CD3+ T cells or neutrophils as mediated by NDV-3 were determined in parallel. NDV-3 immunization achieved protective efficacy against MRSA in terms of abscess area, volume, bacterial density and CFU as compared to adjuvant alone. Protective efficacy of NDV-3 corresponded to increases in serum IgG, serum and tissue biomarkers of Th1-Th17 polarization, and corresponding neutrophil infiltration and host defense peptide induction in context of abscesses. These data further demonstrated that NDV-3 immunization induces robust B and T cell mechanisms of protective efficacy against MRSA in context of skin and mucosa.

Results

NDV-3 was efficacious against MRSA as measured by reduced abscess area, volume, and CFU versus adjuvant alone (Table 3). Efficacy as measured by area of dermonecrosis and abscess volume were equivalent for all strains tested. Significant increases in serum IgG, serum and tissue biomarkers of Th1 (INF-γ) and Th17 (IL-17) polarization (Table 3), neutrophil infiltration (Ly6G), IL-22 elaboration, as well as mβD-3 induction were correlated with NDV-3 protective efficacy (FIGS. 3-8).

TABLE 3

NDV-3 efficacy and immune response vs. MRSA Xen30 in murine SSSI.

|  | Control | 3 μg | 10 μg | 100 μg |
|---|---|---|---|---|
| Abscess |  |  |  |  |
| Area d7 | 1.88 cm$^2$ | 1.47 cm$^{2*}$ | 1.59 cm$^{2*}$ | 0.77 cm$^{2\dagger\dagger}$ |
| Volume d7 | 1.29 cm$^3$ | 0.95 cm$^{3*}$ | 0.96 cm$^{3**}$ | 0.38 cm$^{3\dagger\dagger}$ |
| Flux d7 | 3.22 × 10$^5$ | 1.48 × 10$^{5*}$ | 2.15 × 10$^{5\ *}$ | 1.06 × 10$^{5**}$ |
| Geo Mean | 7.50 | 6.23$^\dagger$ | 6.68$^\dagger$ | 6.05$^\dagger$ |
| Log CFU | (8.0/7.4)$^a$ | (6.4/6.1) | (6.8/6.4) | (6.2/5.6) |
| d7 IM | [n = 54] | [n = 20] | [n = 20] | [n = 20] |

TABLE 3-continued

NDV-3 efficacy and immune response vs. MRSA Xen30 in murine SSSI.

|  | Control | 3 μg | 10 μg | 100 μg |
|---|---|---|---|---|
| Analyte |  |  |  |  |
| IgG | 1.0 GCU$^b$ | 44.8 GCU$^{\dagger\dagger}$ | ND | 81.8 GCU$^{\dagger\dagger}$ |
| IFN-γ | 9.5 SFU$^c$ | 12.8 SFU | ND | 34.3 SFU* |
| IL-17 | 18.9 SFU | 132.6 SFU$^{\dagger\dagger}$ | ND | 161.2 SFU** |

$^a$Mean variance
$^b$GCU, geomean/dilution corrected units
$^c$SPU, mean spot forming units/10$^6$ splenocytes
*$P < 0.5$;
**$P < 0.1$;
$^\dagger P < 0.05$;
$^{\dagger\dagger}P < 0.01$ Conclusion NDV-3 induces protective efficacy against MRSA in murine SSSI. Immunologic mechanisms of efficacy included robust B and T cell responses consistent with Th1-Th17 paradigms in which neutrophils and host defense peptides are targeted and coordinated in context of infection.

Example 3

Figure 9:
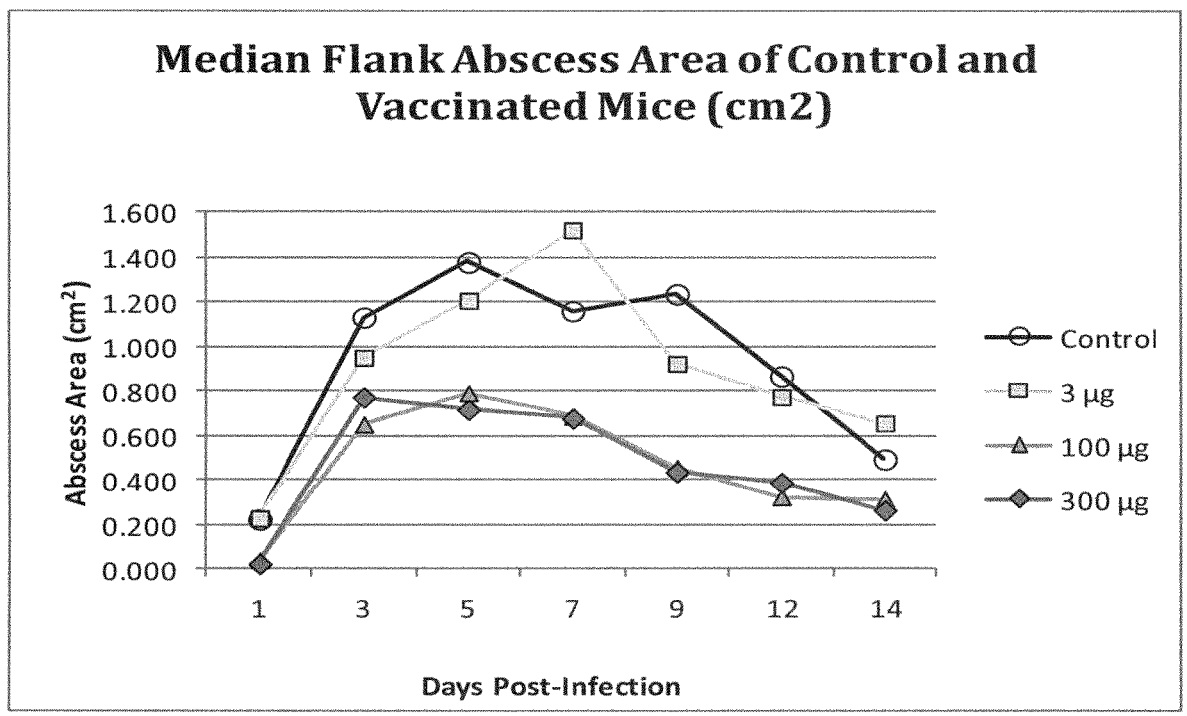
FIG. 9 is a chart showing the median flank abscess area of control and vaccinated mice.
Figure 10:
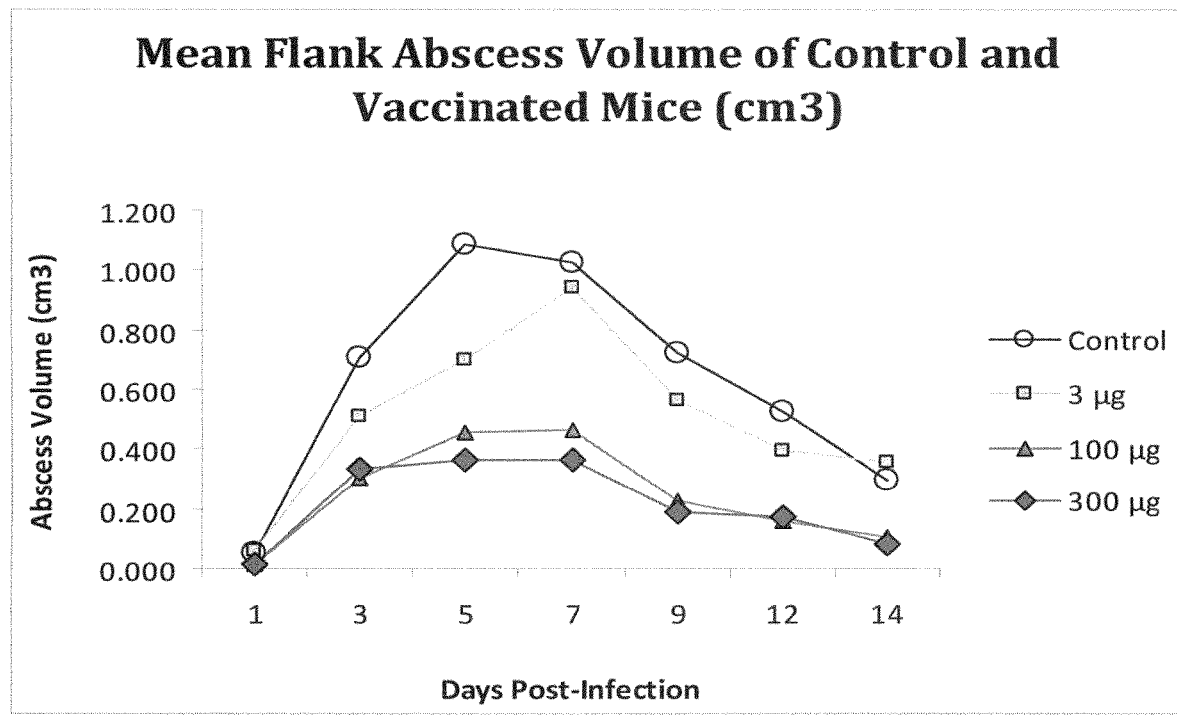
FIG. 10 is a chart showing the median flank abscess volume of control and vaccinated mice.

An additional set of experiments was conducted to evaluate the efficacy of the NDV-3 vaccine in a murine model of SSSI due to Xen30 MRSA and comparative strains of MRSA. Experiments were conducted as described in Examples 1 and 2. Median data kinetics of vaccine efficacy versus time is shown in FIG. 9 (median flank abscess area of control and vaccinated mice) and FIG. 10 (mean flank abscess volume of control and vaccinated mice). These data confirm that vaccination with NDV-3 suppresses evolution of the abscess, particularly at dosages greater than 3 μg.

Figure 11:
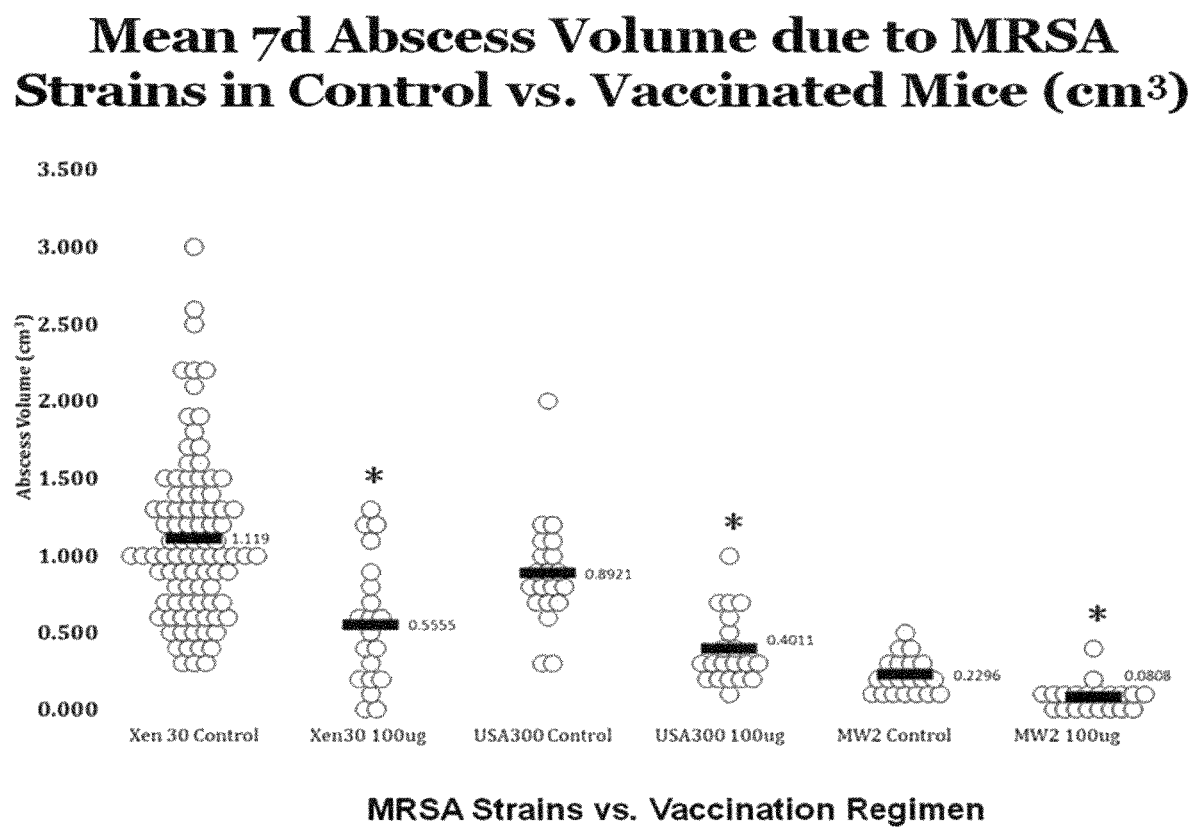
FIG. 11 is a chart showing the mean abscess volume due to MRSA strains in control and vaccinated mice at day 7 post-infection. Asterisks indicate significant reduction as compared to respective control.

In addition, efficacy of the vaccine was tested against three different MRSA strains: Xen 30, USA300, and MW2. For each MRSA strain, a negative control and a 100 μg dosage group were tested. The mean lesion volume at day 7 post-infection was determined, as shown in FIG. 11. Each strain was the same inoculum ($2 \times 10^7$). MW2 exhibited low virulence in these experiments.

The data demonstrate that regardless of MRSA strain tested, the NDV-3 vaccine has equivalent efficacy (e.g., about 50% reduction) in restricting abscess volume. Thus, NDV-3 efficacy is not MRSA strain-specific.

Example 4

Figure 12:
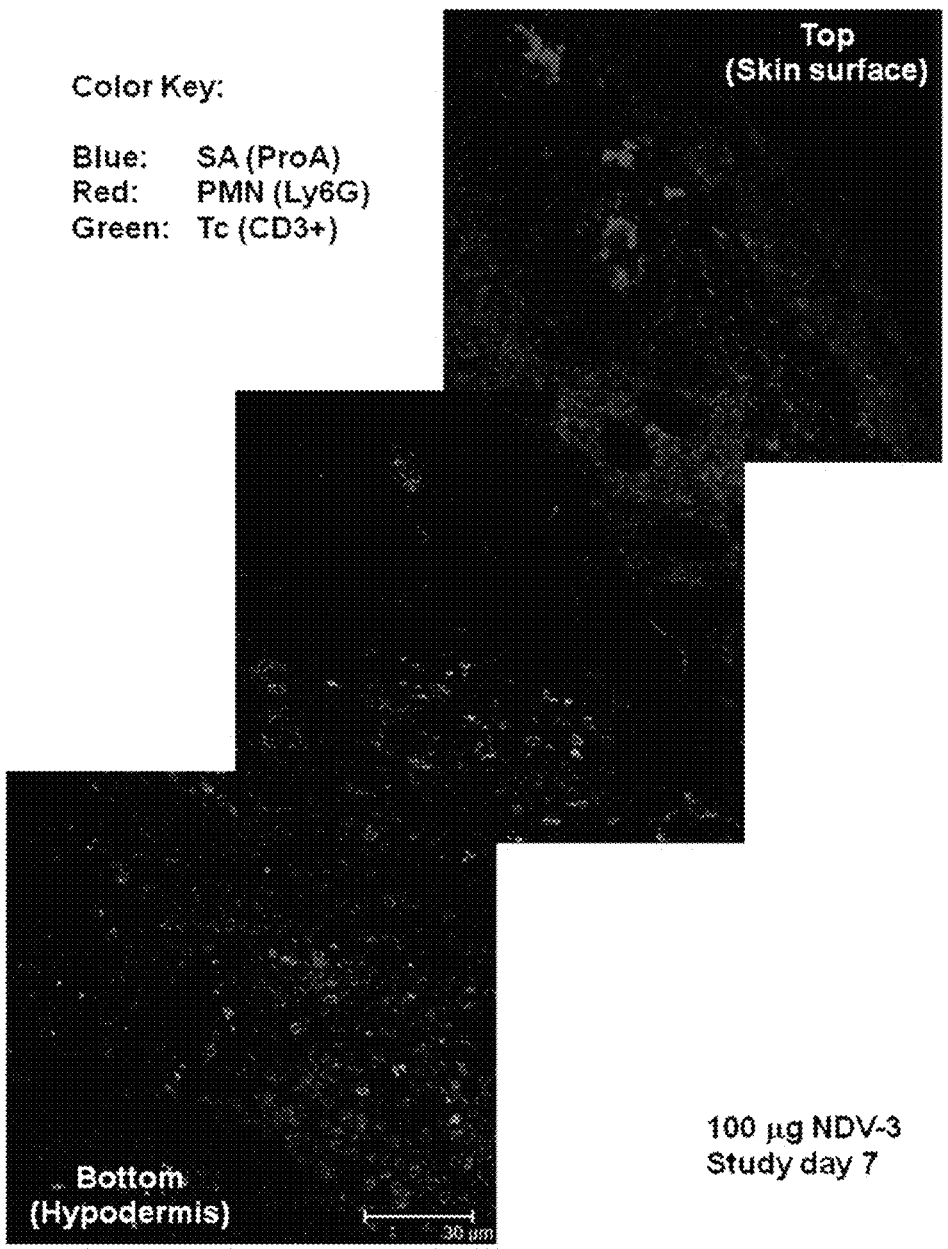
FIG. 12 is a composite immunofluorescence image of a MRSA abscess from a NDV-3 (100 µg) vaccinated mouse.

In a further set of experiments, composite immunofluorescence images of MRSA abscesses were recorded and analyzed. FIG. 12 is a composite immunofluorescence image of a representative MRSA abscess from a NDV-3 (100 μg) vaccinated mouse, and FIG. 13 is a composite immunofluorescence image of a representative MRSA abscess from a control mouse.

In each of the above images, each component of the image is of the same lesion, magnified approximately 500-fold. As immunofluorescence signal is difficult to resolve at low power, images were recorded for each section of the lesion at higher power, moving from the epidermis of the skin, into the subdermis, and down into the hypodermis. Thus, the components are merged to illustrate a continuous immunofluorescence map of *S. aureus* (blue), neutrophils (red), and CD3+ (T cells) green, throughout a lesion and maintaining magnification sufficient for resolution of immunofluorescence. The image components represent a function of high-power fields positioned to systematically capture equivalent areas in the NDV-3 and control lesions for head-to-head comparison of abscess immunophenotypes.

Figure 13:
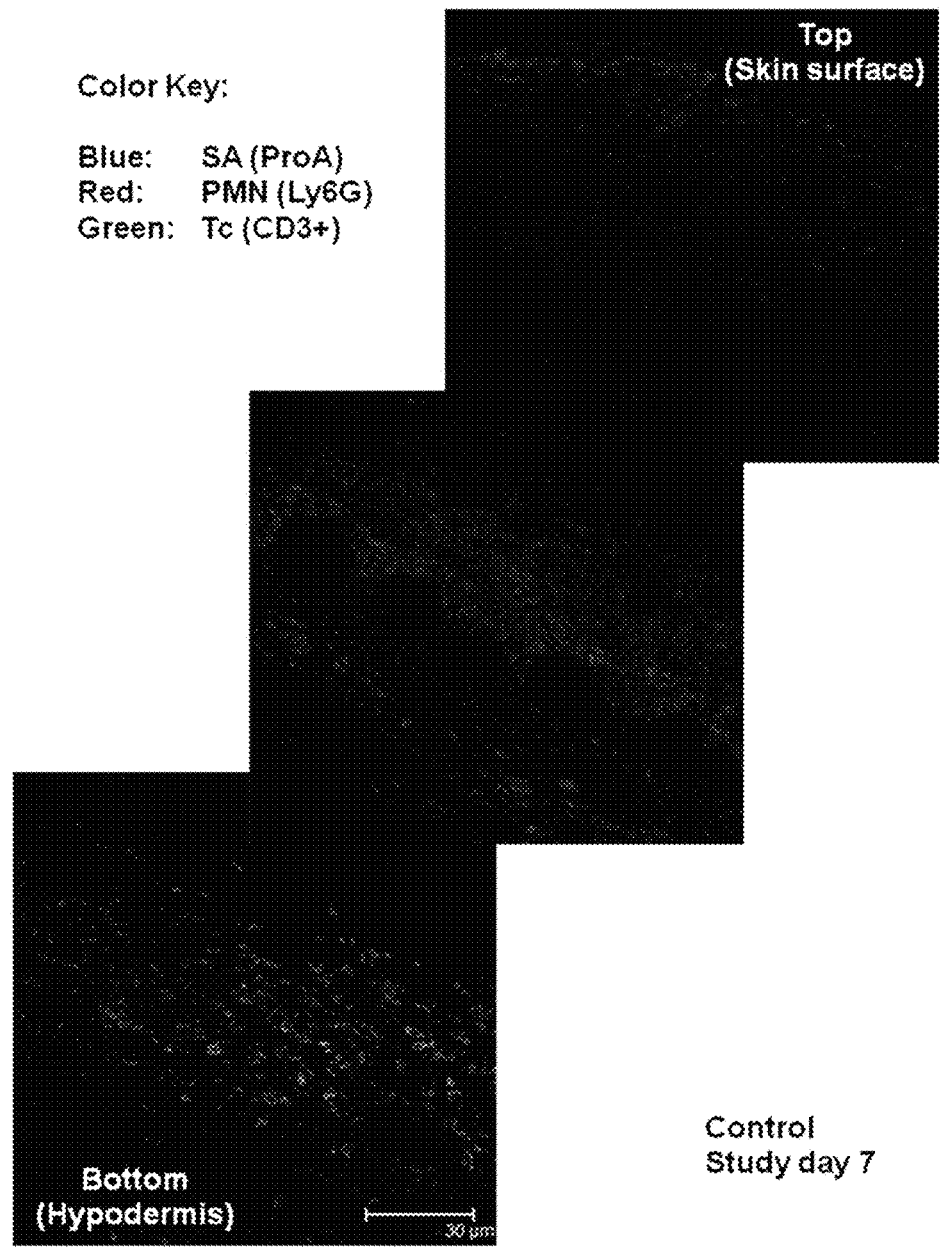
FIG. 13 is a composite immunofluorescence image of a MRSA abscess from a control mouse.

As FIGS. 12 and 13 reveal, in the NDV-3 vaccinated abscess, there are few MRSA organisms (blue), and they are restricted to the epidermis, with infiltration of neutrophils (red) mediated by an influx of CD3+ T cells (green). In contrast, in the control abscess, there are many MRSA organisms, and they are invasive to two distinct regions (epidermis and hypodermis), corresponding with substantially less neutrophil and CD3+ cell infiltration. While the images shown in FIGS. 12 and 13 are from individual lesions, they are representative of lesions in vaccinated and control groups overall and are consistent with the quantitative findings described in the preceding Examples.

Example 5

The compositions and methods described herein may be used, e.g., to vaccinate a human at risk for the development of a *Staphylococcus aureus* skin or soft tissue infection against *Staphylococcus aureus*. First, a human at risk for the development of an *S. aureus* SSSI is identified. Second, the human is administered an immunogenic amount of a vaccine comprising a polypeptide comprising Als3p, or an immunogenic fragment thereof, in a pharmaceutically acceptable medium. For example, the human is administered between one and three doses of NDV-3 containing between 3 and 1000 µg of the recombinant N-terminus of the *Candida* surface protein Als3 (SEQ ID NO:2) per dose, with multiple doses occurring at intervals of two weeks to six months.

It is expected that, following administration of the vaccine, the human is at decreased risk for the development of an *S. aureus* SSSI for a period lasting from one month to several years or more.

Likewise, a human who is identified as having an *S. aureus* SSSI may be treated by administration of an immunogenic amount of a pharmaceutical composition comprising a polypeptide comprising Als3p, or an immunogenic fragment thereof, in a pharmaceutically acceptable medium. For example, the human is administered between one and three doses of NDV-3 containing between 3 and 1000 µg of the recombinant N-terminus of the *Candida* surface protein Als3 (SEQ ID NO:2) per dose, with multiple doses occurring at intervals of two weeks to six months.

It is expected that, following administration of the pharmaceutical composition, the *S. aureus* SSSI of the human is decreased in severity.

Example 6

The compositions and methods described herein may be used, e.g., to vaccinate a bovine species at risk for the development of a *Staphylococcus aureus* skin or soft tissue infection against *Staphylococcus aureus*. In particular, the bovine species may be at risk of developing bovine mastitis caused by *S. aureus*. First, a bovine species at risk for the development of an *S. aureus* SSSI, e.g., bovine mastitis, is identified. For example, any milk-producing bovine may be considered to be at risk of developing bovine mastitis caused by *S. aureus*. Second, the bovine species is administered an immunogenic amount of a vaccine comprising a polypeptide comprising Als3p, or an immunogenic fragment thereof, in a pharmaceutically acceptable medium. For example, the bovine species is administered between one and three doses of NDV-3 containing between 3 and 1000 µg of the recombinant N-terminus of the *Candida* surface protein Als3 (SEQ ID NO:2) per dose, with multiple doses occurring at intervals of two weeks to six months.

It is expected that, following administration of the vaccine, the bovine species is at decreased risk for the development of an *S. aureus* SSSI, e.g., bovine mastitis.

Likewise, a bovine species identified as having an *S. aureus* SSSI, e.g., bovine mastitis, may be treated by administration of an immunogenic amount of a pharmaceutical composition comprising a polypeptide comprising Als3p, or an immunogenic fragment thereof, in a pharmaceutically acceptable medium. For example, the bovine species is administered between one and three doses of NDV-3 containing between 3 and 1000 µg of the recombinant N-terminus of the *Candida* surface protein Als3 (SEQ ID NO:2) per dose, with multiple doses occurring at intervals of two weeks to six months.

It is expected that, following administration of the pharmaceutical composition, the *S. aureus* SSSI, e.g., bovine mastitis, of the bovine species is decreased in severity.

Other Embodiments

All publications and patents cited in this specification are incorporated herein by reference as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A method of treating a skin abscess caused by *Staphylococcus aureus* in a human in need thereof comprising administering to said human an effective amount of an immunogenic composition comprising 30 to 300 micrograms of an isolated polypeptide consisting of the N-terminal domain of *Candida albicans* agglutinin-like sequence 3 protein (Als3p), wherein the N-terminal domain extends from the end of the signal peptide to the beginning of the tandem repeats of the *Candida albicans* Als3p, in a pharmaceutically acceptable medium, wherein the composition elicits an immune response in said human against the *S. aureus* that decreases the area and severity of the skin abscess.

2. The method of claim 1, wherein the amino acid sequence of said N-terminal domain of the Als3p consists of SEQ ID NO: 2.

3. The method of claim 1, wherein said *S. aureus* is a methicillin-resistant strain of *S. aureus* (MRSA).

4. The method of claim 1, wherein said *S. aureus* is a methicillin-sensitive strain of *S. aureus* (MSSA).

5. The method of claim 1, wherein said *S. aureus* is a vancomycin-resistant strain of *S. aureus* (VRSA) or a daptomycin-resistant strain of *S. aureus* (DRSA).

6. The method of claim 1, wherein said polypeptide is conjugated to a carrier.

7. The method of claim 6, wherein said carrier is keyhole limpet hemocyanin (KLH), CRM197, tetanus toxoid, diphtheria toxoid, or *Neisseria meningitidis* outer membrane protein complex.

8. The method of claim 6, wherein said carrier is a phage, a yeast, a virus, a virosome, or a recombinant virus-like particle.

9. The method of claim 1, wherein said immunogenic composition is administered by intramuscular, subcutaneous, intradermal, or sublingual administration, or is administered for inhalation in a microparticulate formulation.

10. The method of claim 1, wherein said method further comprises administering a booster dose of the immunogenic composition to said human.

11. The method of claim 1, wherein said immunogenic composition comprises an immunostimulating adjuvant.

12. The method of claim 1, further comprising administering an antibiotic.

13. The method of claim 12, wherein said antibiotic is co-formulated or co-administered with said immunogenic composition.

14. The method of claim 1, wherein the immunogenic composition comprises 30 micrograms of the polypeptide.

15. The method of claim 1, wherein the immunogenic composition comprises 300 micrograms of the polypeptide.

16. The method of claim 1, wherein the immunogenic composition is administered at a volume of 0.5 ml in phosphate-buffered saline of pH 7.

17. The method of claim 1, wherein one to three doses of the immunogenic composition is administered to the human.

* * * * *

SEQUENCE LISTING

```
<160> NUMBER OF SEQ ID NOS: 3

<210> SEQ ID NO 1
<211> LENGTH: 1119
<212> TYPE: PRT
<213> ORGANISM: Candida albicans
<220> FEATURE:
<221> NAME/KEY: PROTEIN
<222> LOCATION: (1)..(1119)
<223> OTHER INFORMATION: Agglutinin-like sequence 3 protein (Als3p)

<400> SEQUENCE: 1

Met Leu Gln Gln Tyr Thr Leu Leu Leu Ile Tyr Leu Ser Val Ala Thr
1               5                   10                  15
```

-continued

Ala Lys Thr Ile Thr Gly Val Phe Asn Ser Phe Asn Ser Leu Thr Trp
         20                  25                  30

Ser Asn Ala Ala Thr Tyr Asn Tyr Lys Gly Pro Gly Thr Pro Thr Trp
         35                  40                  45

Asn Ala Val Leu Gly Trp Ser Leu Asp Gly Thr Ser Ala Ser Pro Gly
         50                  55                  60

Asp Thr Phe Thr Leu Asn Met Pro Cys Val Phe Lys Phe Thr Thr Ser
65                   70                  75                  80

Gln Thr Ser Val Asp Leu Thr Ala His Gly Val Lys Tyr Ala Thr Cys
                 85                  90                  95

Gln Phe Gln Ala Gly Glu Glu Phe Met Thr Phe Ser Thr Leu Thr Cys
             100                 105                 110

Thr Val Ser Asn Thr Leu Thr Pro Ser Ile Lys Ala Leu Gly Thr Val
         115                 120                 125

Thr Leu Pro Leu Ala Phe Asn Val Gly Gly Thr Gly Ser Ser Val Asp
         130                 135                 140

Leu Glu Asp Ser Lys Cys Phe Thr Ala Gly Thr Asn Thr Val Thr Phe
145                 150                 155                 160

Asn Asp Gly Gly Lys Lys Ile Ser Ile Asn Val Asp Phe Glu Arg Ser
                 165                 170                 175

Asn Val Asp Pro Lys Gly Tyr Leu Thr Asp Ser Arg Val Ile Pro Ser
             180                 185                 190

Leu Asn Lys Val Ser Thr Leu Phe Val Ala Pro Gln Cys Ala Asn Gly
         195                 200                 205

Tyr Thr Ser Gly Thr Met Gly Phe Ala Asn Thr Tyr Gly Asp Val Gln
         210                 215                 220

Ile Asp Cys Ser Asn Ile His Val Gly Ile Thr Lys Gly Leu Asn Asp
225                 230                 235                 240

Trp Asn Tyr Pro Val Ser Ser Glu Ser Phe Ser Tyr Thr Lys Thr Cys
             245                 250                 255

Ser Ser Asn Gly Ile Phe Ile Thr Tyr Lys Asn Val Pro Ala Gly Tyr
         260                 265                 270

Arg Pro Phe Val Asp Ala Tyr Ile Ser Ala Thr Asp Val Asn Ser Tyr
         275                 280                 285

Thr Leu Ser Tyr Ala Asn Glu Tyr Thr Cys Ala Gly Gly Tyr Trp Gln
         290                 295                 300

Arg Ala Pro Phe Thr Leu Arg Trp Thr Gly Tyr Arg Asn Ser Asp Ala
305                 310                 315                 320

Gly Ser Asn Gly Ile Val Ile Val Ala Thr Thr Arg Thr Val Thr Asp
                 325                 330                 335

Ser Thr Thr Ala Val Thr Thr Leu Pro Phe Asp Pro Asn Arg Asp Lys
             340                 345                 350

Thr Lys Thr Ile Glu Ile Leu Lys Pro Ile Pro Thr Thr Thr Ile Thr
         355                 360                 365

Thr Ser Tyr Val Gly Val Thr Thr Ser Tyr Ser Thr Lys Thr Ala Pro
         370                 375                 380

Ile Gly Glu Thr Ala Thr Val Ile Val Asp Ile Pro Tyr His Thr Thr
385                 390                 395                 400

Thr Thr Val Thr Ser Lys Trp Thr Gly Thr Ile Thr Ser Thr Thr Thr
                 405                 410                 415

His Thr Asn Pro Thr Asp Ser Ile Asp Thr Val Ile Val Gln Val Pro
             420                 425                 430

```
Ser Pro Asn Pro Thr Val Thr Thr Glu Tyr Trp Ser Gln Ser Phe
        435                 440                 445

Ala Thr Thr Thr Thr Ile Thr Gly Pro Pro Gly Asn Thr Asp Thr Val
450                 455                 460

Leu Ile Arg Glu Pro Pro Asn His Thr Val Thr Thr Thr Glu Tyr Trp
465                 470                 475                 480

Ser Glu Ser Tyr Thr Thr Thr Ser Thr Phe Thr Ala Pro Pro Gly Gly
                485                 490                 495

Thr Asp Ser Val Ile Ile Lys Glu Pro Pro Asn Pro Thr Val Thr Thr
                500                 505                 510

Thr Glu Tyr Trp Ser Glu Ser Tyr Thr Thr Thr Ser Thr Phe Thr Ala
                515                 520                 525

Pro Pro Gly Gly Thr Asp Ser Val Ile Ile Lys Glu Pro Pro Asn His
                530                 535                 540

Thr Val Thr Thr Thr Glu Tyr Trp Ser Gln Ser Tyr Thr Thr Thr Thr
545                 550                 555                 560

Thr Val Thr Ala Pro Pro Gly Gly Thr Asp Thr Val Leu Val Arg Glu
                565                 570                 575

Pro Pro Asn His Thr Val Thr Thr Thr Glu Tyr Trp Ser Gln Ser Tyr
                580                 585                 590

Thr Thr Thr Thr Thr Val Ile Ala Pro Pro Gly Gly Thr Asp Ser Val
                595                 600                 605

Ile Ile Arg Glu Pro Pro Asn Pro Thr Val Thr Thr Thr Glu Tyr Trp
                610                 615                 620

Ser Gln Ser Tyr Ala Thr Thr Thr Ile Thr Ala Pro Pro Gly Glu
625                 630                 635                 640

Thr Asp Thr Val Leu Ile Arg Glu Pro Pro Asn His Thr Val Thr Thr
                645                 650                 655

Thr Glu Tyr Trp Ser Gln Ser Tyr Ala Thr Thr Thr Ile Thr Ala
                660                 665                 670

Pro Pro Gly Glu Thr Asp Thr Val Leu Ile Arg Glu Pro Pro Asn His
                675                 680                 685

Thr Val Thr Thr Thr Glu Tyr Trp Ser Gln Ser Phe Ala Thr Thr Thr
                690                 695                 700

Thr Val Thr Ala Pro Pro Gly Gly Thr Asp Thr Val Ile Ile Arg Glu
705                 710                 715                 720

Pro Pro Asn His Thr Val Thr Thr Thr Glu Tyr Trp Ser Gln Ser Tyr
                725                 730                 735

Ala Thr Thr Thr Ile Thr Ala Pro Pro Gly Glu Thr Asp Thr Val
                740                 745                 750

Leu Ile Arg Glu Pro Pro Asn His Thr Val Thr Thr Thr Glu Tyr Trp
                755                 760                 765

Ser Gln Ser Tyr Ala Thr Thr Thr Ile Ile Ala Pro Pro Gly Glu
                770                 775                 780

Thr Asp Thr Val Leu Ile Arg Glu Pro Pro Asn Pro Thr Val Thr Thr
785                 790                 795                 800

Thr Glu Tyr Trp Ser Gln Ser Tyr Thr Thr Ala Thr Val Thr Ala
                805                 810                 815

Pro Pro Gly Gly Thr Asp Thr Val Ile Ile Tyr Asp Thr Met Ser Ser
                820                 825                 830

Ser Glu Ile Ser Ser Phe Ser Arg Pro His Tyr Thr Asn His Thr Thr
                835                 840                 845

Leu Trp Ser Thr Thr Trp Val Ile Glu Thr Lys Thr Ile Thr Glu Thr
```

```
                850                 855                 860

Ser Cys Glu Gly Asp Lys Gly Cys Ser Trp Val Ser Val Ser Thr Arg
865                 870                 875                 880

Ile Val Thr Ile Pro Asn Asn Ile Glu Thr Pro Met Val Thr Asn Thr
                885                 890                 895

Val Asp Ser Thr Thr Glu Ser Thr Ser Gln Ser Pro Ser Gly Ile
                900                 905                 910

Phe Ser Glu Ser Gly Val Ser Val Glu Thr Glu Ser Thr Val Thr
            915                 920                 925

Thr Ala Gln Thr Asn Pro Ser Val Pro Thr Thr Glu Ser Glu Val Val
    930                 935                 940

Phe Thr Thr Lys Gly Asn Asn Glu Asn Gly Pro Tyr Glu Ser Pro Ser
945                 950                 955                 960

Thr Asn Val Lys Ser Ser Met Asp Glu Asn Ser Glu Phe Thr Thr Ser
                965                 970                 975

Thr Ala Ala Ser Thr Ser Thr Asp Ile Glu Asn Glu Thr Ile Ala Thr
                980                 985                 990

Thr Gly Ser Val Glu Ala Ser Ser Pro Ile Ile Ser Ser Ser Ala Asp
        995                 1000                1005

Glu Thr Thr Thr Val Thr Thr Thr Ala Glu Ser Thr Ser Val Ile
    1010                1015                1020

Glu Gln Pro Thr Asn Asn Asn Gly Gly Gly Lys Ala Pro Ser Ala
    1025                1030                1035

Thr Ser Ser Pro Ser Thr Thr Thr Thr Ala Asn Asn Asp Ser Val
    1040                1045                1050

Ile Thr Gly Thr Thr Ser Thr Asn Gln Ser Gln Ser Gln Ser Gln
    1055                1060                1065

Tyr Asn Ser Asp Thr Gln Gln Thr Thr Leu Ser Gln Gln Met Thr
    1070                1075                1080

Ser Ser Leu Val Ser Leu His Met Leu Thr Thr Phe Asp Gly Ser
    1085                1090                1095

Gly Ser Val Ile Gln His Ser Thr Trp Leu Cys Gly Leu Ile Thr
    1100                1105                1110

Leu Leu Ser Leu Phe Ile
    1115

<210> SEQ ID NO 2
<211> LENGTH: 416
<212> TYPE: PRT
<213> ORGANISM: Candida albicans
<220> FEATURE:
<221> NAME/KEY: PROTEIN
<222> LOCATION: (1)..(416)
<223> OTHER INFORMATION: Agglutinin-like sequence 3 protein (Als3p)

<400> SEQUENCE: 2

Lys Thr Ile Thr Gly Val Phe Asn Ser Phe Asn Ser Leu Thr Trp Ser
1               5                   10                  15

Asn Ala Ala Thr Tyr Asn Tyr Lys Gly Pro Gly Thr Pro Thr Trp Asn
                20                  25                  30

Ala Val Leu Gly Trp Ser Leu Asp Gly Thr Ser Ala Ser Pro Gly Asp
            35                  40                  45

Thr Phe Thr Leu Asn Met Pro Cys Val Phe Lys Phe Thr Thr Ser Gln
    50                  55                  60

Thr Ser Val Asp Leu Thr Ala His Gly Val Lys Tyr Ala Thr Cys Gln
65                  70                  75                  80
```

Phe Gln Ala Gly Glu Glu Phe Met Thr Phe Ser Thr Leu Thr Cys Thr
                85                  90                  95

Val Ser Asn Thr Leu Thr Pro Ser Ile Lys Ala Leu Gly Thr Val Thr
            100                 105                 110

Leu Pro Leu Ala Phe Asn Val Gly Gly Thr Gly Ser Ser Val Asp Leu
        115                 120                 125

Glu Asp Ser Lys Cys Phe Thr Ala Gly Thr Asn Thr Val Thr Phe Asn
130                 135                 140

Asp Gly Gly Lys Lys Ile Ser Ile Asn Val Asp Phe Glu Arg Ser Asn
145                 150                 155                 160

Val Asp Pro Lys Gly Tyr Leu Thr Asp Ser Arg Val Ile Pro Ser Leu
                165                 170                 175

Asn Lys Val Ser Thr Leu Phe Val Ala Pro Gln Cys Ala Asn Gly Tyr
            180                 185                 190

Thr Ser Gly Thr Met Gly Phe Ala Asn Thr Tyr Gly Asp Val Gln Ile
        195                 200                 205

Asp Cys Ser Asn Ile His Val Gly Ile Thr Lys Gly Leu Asn Asp Trp
210                 215                 220

Asn Tyr Pro Val Ser Ser Glu Ser Phe Ser Tyr Thr Lys Thr Cys Ser
225                 230                 235                 240

Ser Asn Gly Ile Phe Ile Thr Tyr Lys Asn Val Pro Ala Gly Tyr Arg
                245                 250                 255

Pro Phe Val Asp Ala Tyr Ile Ser Ala Thr Asp Val Asn Ser Tyr Thr
            260                 265                 270

Leu Ser Tyr Ala Asn Glu Tyr Thr Cys Ala Gly Tyr Trp Gln Arg
        275                 280                 285

Ala Pro Phe Thr Leu Arg Trp Thr Gly Tyr Arg Asn Ser Asp Ala Gly
290                 295                 300

Ser Asn Gly Ile Val Ile Val Ala Thr Thr Arg Thr Val Thr Asp Ser
305                 310                 315                 320

Thr Thr Ala Val Thr Thr Leu Pro Phe Asp Pro Asn Arg Asp Lys Thr
                325                 330                 335

Lys Thr Ile Glu Ile Leu Lys Pro Ile Pro Thr Thr Thr Ile Thr Thr
            340                 345                 350

Ser Tyr Val Gly Val Thr Thr Ser Tyr Leu Thr Lys Thr Ala Pro Ile
        355                 360                 365

Gly Glu Thr Ala Thr Val Ile Val Asp Ile Pro Tyr His Thr Thr Thr
370                 375                 380

Thr Val Thr Ser Lys Trp Thr Gly Thr Ile Thr Ser Thr Thr Thr His
385                 390                 395                 400

Thr Asn Pro Thr Asp Ser Ile Asp Thr Val Ile Val Gln Val Pro Leu
                405                 410                 415

<210> SEQ ID NO 3
<211> LENGTH: 1251
<212> TYPE: DNA
<213> ORGANISM: Artificial Sequence
<220> FEATURE:
<223> OTHER INFORMATION: Synthetic construct

<400> SEQUENCE: 3
aagacaatca ctggtgtttt caacagtttt aattcattga cttggtctaa tgctgctacg      60
tataattata agggaccagg aaccccaact tggaatgctg ttttgggttg gtctttagat     120
ggtactagtg caagtccggg agatacattc acattgaata tgccatgtgt gtttaaattt     180

```
                                                      -continued actacttctc aaacatctgt tgatttgact gctcatggtg ttaaatatgc tacatgtcaa    240
tttcaggcag gtgaagaatt tatgaccttt tctacattaa catgtactgt gagcaatact    300
ttgactccat ctattaaggc tttgggtact gtcactttac cacttgcatt caatgtaggt    360
ggaactggtt cttctgttga tttggaagat tctaaatgtt ttactgctgg tactaacaca    420
gttacattta atgatggtgg caagaaaatc tcaattaatg ttgattttga aaggtcaaat    480
gtcgatccaa aagggtactt aactgattcc agagttatac caagtctcaa caaagtgtca    540 actcttttg ttgcaccaca atgtgcaaat ggttacacat ctggtacaat gggattcgct     600
aacacttatg gtgatgttca aattgactgt tcaaatattc atgttggtat tacaaaagga    660
ttgaatgatt ggaattatcc ggtttcatct gaatcattta gttacaccaa aacttgttca    720
tctaatggta tctttatcac atataaaaac gttcctgccg gttatcgtcc atttgttgac    780
gcttatattt ctgctacaga tgttaattcg tacaccttgt cgtatgctaa tgaatatact    840
tgtgctggtg gttattggca acgtgcacct ttcacattaa gatggactgg atacagaaat    900
agtgatgctg gatctaacgg tattgttatt gtggctacta ccagaacagt tacagacagt    960
actaccgccg tgaccacctt accattcgat cctaaccgcg acaaaactaa gacaattgaa   1020
attttgaaac ctattccaac aactacaatc acaacatcat atgttggtgt gactacttcc   1080
tacctgacca aaactgcacc aattggggaa actgctactg ttattgttga tattccatat   1140
cacactacca ctactgttac cagtaaatgg acaggaacaa ttacttccac cacaacacat   1200
actaatccaa ctgactcaat agacactgtc attgtacaag ttccactgtg a            1251
```